(12) United States Patent
Coombes et al.

(10) Patent No.: US 8,097,274 B2
(45) Date of Patent: Jan. 17, 2012

(54) SKIN SUBSTITUTES, PREPARATION METHODS AND USES THEREOF

(75) Inventors: Allan Gerald Arthur Coombes, Claygate (GB); Eric Frank Adams, Birmingham (GB); Niann-Tzyy Dai, Taipei (TW); Tsung-Hsun Liu, Taichung (TW); Ming-Kung Yeh, Taipei (TW)

(73) Assignee: National Defense Medical Center, Taipei (TW)

( * ) Notice: Subject to any disclaimer, the term of this patent is extended or adjusted under 35 U.S.C. 154(b) by 118 days.

(21) Appl. No.: 12/447,434

(22) PCT Filed: Oct. 27, 2006

(86) PCT No.: PCT/US2006/042234
§ 371 (c)(1), (2), (4) Date: Jul. 23, 2009

(87) PCT Pub. No.: WO2008/051228
PCT Pub. Date: May 2, 2008

(65) Prior Publication Data
US 2010/0062041 A1    Mar. 11, 2010

(51) Int. Cl.
| | | |
|---|---|---|
| A61K 9/70 | (2006.01) | |
| A61K 31/785 | (2006.01) | |
| A61K 38/00 | (2006.01) | |
| A61K 31/13 | (2006.01) | |
| A61K 31/12 | (2006.01) | |
| A61K 31/04 | (2006.01) | |
| A61K 47/30 | (2006.01) | |
| A61K 45/00 | (2006.01) | |
| A61K 31/74 | (2006.01) | |
| A61F 2/00 | (2006.01) | |
| A61F 2/10 | (2006.01) | |
| A61F 2/02 | (2006.01) | |
| A61L 15/00 | (2006.01) | |
| C12N 5/00 | (2006.01) | |
| C12N 5/07 | (2006.01) | |
| C12N 5/071 | (2006.01) | |
| C12N 5/02 | (2006.01) | |
| C08J 9/00 | (2006.01) | |
| A61P 17/02 | (2006.01) | |

(52) U.S. Cl. ............... 424/443; 424/93.7; 424/78.36; 424/78.38; 424/425; 424/426; 424/444; 424/445; 424/486; 424/78.06; 435/1.1; 435/41; 435/325; 435/347; 435/395; 435/401; 514/579; 514/675; 514/676; 514/740; 514/801; 521/50; 521/62; 521/82; 521/87; 521/90; 521/94; 521/102; 521/134; 521/189; 524/9; 524/10; 525/419; 525/420; 602/52; 602/900; 523/15.12; 523/23.72; 523/23.75; 523/23.76; 523/909; 523/920; 523/925; 523/926

(58) Field of Classification Search .................. 424/443, 424/93.7; 514/772.7; 435/396, 366
See application file for complete search history.

(56) References Cited

U.S. PATENT DOCUMENTS

| | | |
|---|---|---|
| 6,599,323 B2 | 7/2003 | Melican et al. |
| 6,733,530 B1 | 5/2004 | Lam et al. |
| 2003/0072790 A1 | 4/2003 | Tsai et al. |

FOREIGN PATENT DOCUMENTS

| | | |
|---|---|---|
| WO | WO-98/29148 | 7/1998 |
| WO | WO-03/087444 A1 | 10/2003 |
| WO | WO-2006/104901 A2 | 10/2006 |

OTHER PUBLICATIONS

Niann-Tzyy Dai, et al., A co-cultured skin model based on cell support membranes, Biochemical and Biophysical Research Communications 329 (2005) [available on line Feb. 16, 2005], pp. 905-908. (with documentation supporting date) (11 pages total).*

Zhang et al., Electrospinning of Gelatin Fibers and Gelatin/PCL Composite Fibrous Scaffolds, J. Biomed. Mater. Res. B 72, 156-65 (10 pages).*

Zhang et al., Fabrication of porous electrospun nanofibers, Nanotechnology 17 (2006) 901-908 (9 pages).*

Wiley Online Library [Downloaded May 12, 2011] [Retrieved from internet <URL: http://onlinelibrary.wiley.com/doi/10.1002/jbm.b.30128/pdf>], (1 page).*

Seshi et al., Multilineage gene expression in human boen marrow stromal cells as evidenced by single-cell microarray analysis, Blood Cells, Molecules, and Diseases 31 (2003) 268-285 (19 pages w/ cover sheet).*

Wikipedia, Stromal Cells [Downloaded May 11, 2011] [Retrieved from internet <URL: http://en.wikipedia.org/wiki/STromal_cell>], (1 page).*

Dia et al., A co-cultured skin model based on cell support membranes, Biochemical and Biophysical Research Communications, (Apr. 15, 2005), 329 (3): 905-908, (4 pages).*

Ma et al., "Grafting of Gelatin on Electrospun Poly(caprolactone) Nanofibers to Improve Endothelial Cell Spreading and Proliferation and to Control Cell Orientation," Tissue Engineering, vol. 11, No. 7/8, 2005, pp. 1149-1158.

Williamson et al., "Gravity spun polycaprolactone fibres for soft tissue engineering: Interaction with fibroblasts and myoblasts in cell culture," Biomaterials, vol. 27, 2006, pp. 1019-1026.

\* cited by examiner

*Primary Examiner* — Ernst Arnold
*Assistant Examiner* — Miriam A Levin

(74) *Attorney, Agent, or Firm* — Muncy, Geissler, Olds & Lowe, PLLC

(57) ABSTRACT

Provided herein are skin substitutes suitable for use in a living subject for purpose of repairing damaged tissues, methods of producing the skin substitutes and their uses. A biocomposite membrane comprising poly($\epsilon$-caprolactone) (PCL) and at least one material selected from collagen and gelatin is provided. In one embodiment, the biocomposite is a 2-component membrane of PCL and gelatin. In another embodiment, the biocomposite is a 3-component membrane of PCL, collagen and gelatin. The bio-composite membrane may be used directly in vivo as a wound dressing, or as a support for cell growth on each side of the membrane to produce an in vitro cultivated artificial skin for future in vivo and/or in vitro applications.

16 Claims, 26 Drawing Sheets

SKIN SUBSTITUTES, PREPARATION METHODS AND USES THEREOF

FIELD OF THE INVENTION

The present invention relates to skin substitutes for use in a living subject for purpose of repairing damaged tissues, methods of producing the skin substitutes and their uses. More particularly, the present invention provides a biocomposite membrane comprising poly(ε-caprolactone) (PCL) and at least one material selected from collagen and gelatin; an artificial skin prepared by using the biocomposite membrane as a support for cell growth on at least one side of the membrane; preparation methods and uses thereof.

BACKGROUND OF THE INVENTION

Individuals suffer from skin wounds from time to time, and typically, such wounds of a healthy individual would recover within an expected time frame. However, for individuals suffering from burn injuries, trauma, immobility and/or diseases (e.g., diabetics), skin wounds tend to become chronic wounds, which are defined as wounds that do not heal in an expected time frame based on the patient's age, wound location, wound size or wound etiology. Chronic wounds often leave patients at risk for infection, hospitalization and potential amputation of infected limbs, and are becoming a major public health concern. Chronic wounds lead to high rates of morbidity and mortality, diminished quality of life and high healthcare costs. Ideally, conventional wound therapy would result in healing, eliminating the occurrence of chronic wounds, and the need of further intervention. However, in the event of non-healing wounds, more aggressive forms of therapy to promote wound healing, such as application of bio-synthetic dressings, skin substitutes or administration of growth factors, is adopted.

Tissue-engineered skin substitutes (i.e., human skin equivalents) have been developed as products that use living cells (e.g., keratinocytes and fibroblasts) in a scaffold of natural, biodegradable or synthetic matrices to foster wound healing. The scaffold provides a stable framework that guides tissue integration and development. It becomes coated with proteins and lipids, influencing cell migration and adherence. Skin substitutes, also called artificial skin or cellular wound dressings, may be used as temporary or permanent wound coverings, or in conjunction with conventional wound therapy. Some substitutes have a synthetic top layer that eventually peels away or is replaced by new, healthy skin. The bottom layer is composed of a scaffold or matrix, and supports and promotes new cell growth. As the healthy skin, blood vessels, fibroblasts and nerve fibers cross into the matrix, it eventually degrades and disappears. Most commercial available skin substitutes are consisted of sheets of biomaterial matrix with or without allogenic cells contained thereon, which are typically derived from neonatal foreskin; such products include, for example, Alloderm® (Life Cell Inc., Branchburg, N.J.), Integra® (Integra LifeSciences corp., Plainsboro, N.J.), EZ Derm™ (Brennen Medical, Inc., St. Paul, Minn.), Dermagraft® (Smith & Nephew, Inc., Largo, Fla.), Oasis® (Cook Biotech Inc., West Lafayette, Ind.), Apligraft®(Organogenesis, Inc., Canton, Mass.), and OrCel™ (Ortec International, Inc., New York, N.Y.), just to name a few.

Known, conventional materials suitable as a scaffold for cell growth while exhibiting acceptable absorption rates in the living body include natural and synthetic polymers such as collagen, gelatin, hyaluronic acid, pectin and cellulose derivatives. However, scaffolds manufactured by these materials have disadvantages such as relatively high tissue rejecting reactivity, weak mechanical properties and/or difficult to control their decomposition property. A short review on some of the improved materials and/or methods of producing skin substitutes developed by various research teams throughout the world is provided below.

U.S. Pat. No.: 6,599,323 B2 disclosed a biocompatible tissue implant, as well as methods for making and using such an implant. The tissue implant comprises one or more layers of bioabsorbable polymeric foam having pores with an open cell structure. The foam component is reinforced with a material such as a mesh having a density in the range of about 12 to 80%. The foam component is formed from an elastomeric copolymer selected form the group consisting of ε-caprolactone-co-glycolide, ε-caprolactone-co-lactide, p-dioxanone (1,4-dioxan-2-one)-co-lactide, ε-caprolactone-co-p-dioxanone, p-dioxanone-co-trimethylene carbonate, trimethylene carbonate-co-glycolide, trimethylene carbonate-co-lactide, and combinations thereof. The mesh is formed from fibers made from a material selected from the group consisting of polylactic acid, polyglycolic acid, polycaprolactone, polydioxanone, trimethylene carbonate, polyvinyl alcohol, copolymers thereof and combinations thereof.

U.S. Pat. No.: 6,733,530 is related to a skin material for engrafting onto a neodermis of a human patient, said material comprises a composite of: a biosynthetic substratum of an esterified hyaluronic acid, a layer of viable human dermal fibroblasts on an upper side of said biosynthetic substratum, and a layer of viable human keratinocytes over said dermal fibroblast upon said upper side of said biosynthetic substratum, said keratinocytes having been harvested from said patient.

U.S. Pat. No.: 6,974,679 B2 is related to a composite product forming a collagen support comprising at least one porous collagen layer covered on at least one side with an essentially compact collagen membrane consisting either of a collagen film prepared by drying a collagen gel, in air or in a gaseous fluid, or of a highly compressed collagen sponge.

U.S. Pat. No.: 6,946,143 B2 disclosed a biocompatible medical material and porous scaffold for use in tissue engineering, made from a biodegradable glycolide/ε-caprolactone copolymer with a molecular weight of about 10,000 daltons or more, and the molar ratio of glycolide:ε-caprolactone in the copolymer is about 4.0:6.0 to 6.0:4.0. The biodegradable polymer has low immunity, excellent mechanical properties and negligible toxicity, and is suitable for regeneration of soft tissues such as skin and blood vessel, and medical materials such as medical matrix and wound coverings.

U.S. Pat. No.: 6,991,652 B2 is related to a composite for use in a living subject, which comprises a biocompatible 3-dimensional construct comprising: a material selected from the group consisting of alginate, collagen, polylactide, polyethylene glycol, polycaprolactone, polycolide, polydioxanone, and derivatives and copolymers thereof and having a size greater than about 1.5 mm in diameter distributed within a carrier; said carrier comprising a gel matrix or viscous fluid, said gel matrix or said viscous fluid is selected from the group consisting of biodegradable materials and non-biodegradable materials, each having a viscosity of from 10 to 1000 cps; and cells disposed in said biocompatible 3-dimensional construct; wherein the 3-dimensional construct allows for the growth of cells disposed therein and for the ingrowth and attachment of surrounding tissue cells of the living subject.

U.S. Pat. No.: 6,846,675 B2 is related to an in vitro cultured skin substitutes with improved barrier function, which in some cases, is a result of improved culture conditions, while in other cases, is a result from genetic modification of keratinocytes. The skin substitutes thus prepared is useful for irritancy testing.

Inventors of this application had previously identified a biocomposite comprising collagen and PCL as a substrate for growth of skin cells (Dai et al., Biomaterials 25 (2004) 4263-4271; and Dai et al., Biochemical and Biophysical Research Communications 329 (2005) 905-908). For many years, collagen has been proven to be an irreplaceable substrate for the production of artificial skin substitutes containing living cells; however, collagen-based matrices are highly susceptible to bacterial and enzymatic attack and are generally unsuccessful when applied to chronic wounds heavily colonized with bacteria. Hence, there exist in this art a need to develop a biomaterial that is relatively inexpensive than any current biomaterials employed while exhibiting good mechanical strength, biological properties favorable to cell development and metabolism, and low susceptibility to bacterial and enzymatic degradation.

SUMMARY

The objects of this invention are to provide skin substitutes for use in a living subject for purpose of repairing damaged tissues, a method of preparing the skin substitutes and their uses.

Thus, in one aspect, this invention provides a biocomposite membrane comprising poly(ε-caprolactone) and at least one material selected from collagen and gelatin, in a weight ratio between 4:1 to 20:1. In one preferred embodiment, the biocomposite membrane comprises poly(ε-caprolactone) and gelatin. In another preferred embodiment, the biocomposite membrane comprises poly(ε-caprolactone), collagen and gelatin, in which the weight ratio of collagen and poly(ε-caprolactone) or the weight ratio of gelatin/collagen and poly(ε-caprolactone) is between 1:4 to 1:20. The biocomposite membrane is useful as a wound dressing or living organ coverage to promote wound healing and/or tissue regeneration, in particular, for treating subjects with ear drum defect, disruption of tendon/nerve, and/or skin damage that includes burn injuries, ulcers, impaired pigmentation, excisions or other dermatological conditions.

In another aspect, this invention provides a biocomposite product comprising the biocomposite membrane, and at least one layer of cells grown on at least one side of the membrane. The biocomposite product may comprise one layer of cells grown on one side of the biocomposite membrane. Alternatively, the biocomposite product may comprise two layers of cells, with each layer being grown on one side of the biocomposite membrane. In one preferred example, there provides a biocomposite product comprising the biocomposite membrane, a first layer of cells grown on one side of the membrane and a second layer of cells grown on the other side of the membrane. The cells may be selected from fibroblasts, keratinocytes, melanocytes, cells originated from hair follicle and/or sweat gland, endothelial cells originated from the blood, blood cells, chondrocytes, osteocytes, osteoblasts and stem cells originated from the cord blood and/or bone marrow, and the cells may be normal, genetically modified or malignant. In one preferred embodiment, the biocomposite product is an artificial skin, comprising a biocomposite membrane with a layer of keratinocytes grown on one side of the membrane and a layer of fibroblasts grown on the other side of the biocomposite membrane.

In a further aspect, this invention provides a method of cultivating an artificial skin for grafting onto a subject in need of skin treatment and/or wound coverage, comprising growing a layer of keratinocytes on one side of the biocomposite membrane, and growing a layer of fibroblasts on the other side of the biocomposite membrane. The step of growing a layer of keratinocytes may be performed before or after the step of growing a layer of fibroblasts.

In another aspect, this invention provides a method of treating a subject in need of skin treatment and/or wound coverage, comprising applying a biocomposite membrane or an artificial skin onto the subjects having ear drum defect, disruption of tendon/nerve, and/or skin damage that includes burn injuries, ulcers, impaired pigmentation, excisions or other dermatological conditions.

These and other aspects and advantages will become apparent by reference to the following description in conjunction with the accompanying drawings and examples. It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE INVENTION

Figure 1A:
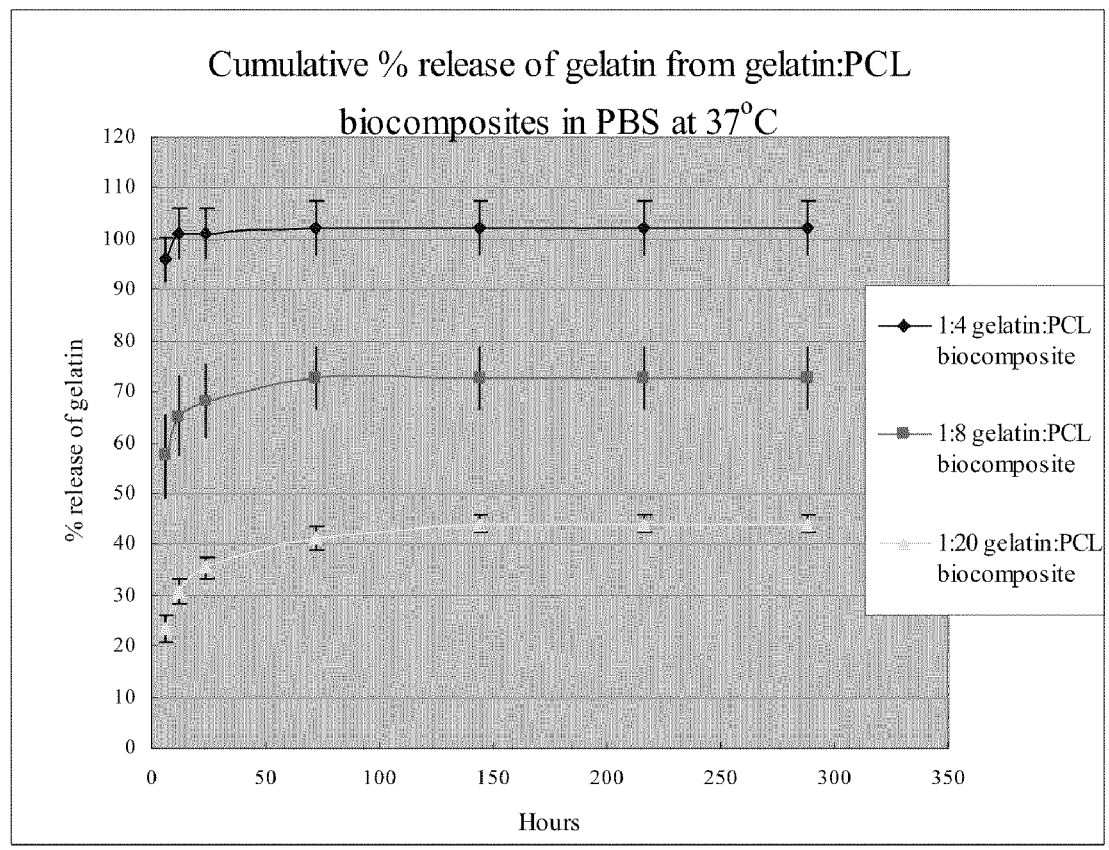
FIG. 1 illustrates the cumulative release of protein from biocomposites of (A) Example 1.2 and (B) Example 1.3 in PBS at 37□ in accordance with one preferred embodiment of this invention.

Reference now will be made in detail to the embodiments of the invention, one or more examples of which are set forth below. The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

The singular forms "a", "and", and "the" are used herein to include plural referents unless the context clearly dictates otherwise.

Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

The present invention is related to in vitro preparation of skin substitutes and in vitro and/or in vivo use of these in vitro cultivated skin substitutes for repairing damaged tissues, particularly, skin tissues. In some embodiment, the in vitro cultivated skin substitute is an acellular biocomposite membrane comprising poly(ε-caprolactone) (PCL) and at least one material selected from collagen and gelatin. In some embodiments, the in vitro cultivated skin substitute comprises cells cultivated on at least one side of the biocomposite membrane. In still other embodiments, the present invention provides in vivo use of the cultivated skin substitutes (acellular biocomposite membrane or artificial skin) for engrafting onto subjects having ear drum defect, disruption of tendon/nerve, and skin damages such as burn injuries, ulcers, impaired pigmentation, excisions or other dermatological conditions.

The term "biocomposite" used herein refers to a material that is biocompatible and suitable for use in this invention without substantially adversely affecting any desire characteristics of the cells to be seeded on the surfaces of the biocomposite or the cells or tissues in the area of a living subject where the biocomposite or a skin substitute comprising the biocomposite to be engrafted on.

Thus, in one embodiment, this invention provides a biocomposite membrane comprises PCL and at least one material selected from collagen and gelatin, in a weight ratio of 4:1 to 20:1, and more preferably between 8:1 to 20:1. In a more preferred embodiment, the biocomposite membrane comprises PCL and gelatin. In another preferred embodiment, the biocomposite membrane comprises PCL, collagen and gelatin, in which the weight ratio of collagen and PCL or the weight ratio of gelatin/collagen and PCL is between 1:4 to 1:20, and more preferably between 1:8 to 1:20.

The biocomposite membrane is prepared by mixing freeze-dried collagen mats or gelatin mats or gelatin/collagen mats slowly with PCL solution, followed by evaporating the solvent to form a 2-component or 3-component membrane in accordance with the method described in Example 1. The 2-component membrane comprises either collagen and PCL, or gelatin and PCL, and the 3-component membrane comprises collagen, gelatin and PCL.

In one preferred example, the biocomposite membrane prepared in accordance with the method described in this invention is used directly in vivo, onto a living subject as a wound dressing or living organ coverage to promote wound healing and/or tissue regeneration, in particularly, for repairing ear drum defect, disruption of tendon/nerve and/or skin damages that includes, but are not limited to, burn injuries, ulcers, impaired pigmentation, excisions or other dermatological conditions. This novel dressing is easy to use. It does not require surgery for its application and can be configured to use on both shallow wounds and deep cavity wounds. The dressing has no living cells and/or rapidly degraded components, accordingly, is easily stored and can be stored in a sterile condition for a period of up to one year. Because the dressing does not require living cells and may use a less expensive material, gelatin, in place of collagen, hence it is easy and inexpensive to produce.

The biocomposite membrane may also be used as a scaffold to support in vitro cell growth on at least one of its surfaces. The biocomposite membrane may comprise one layer of cells grown on one of its surfaces. Alternatively, the biocomposite membrane may comprise two layers of cells, with each layer being grown on one surface of the membrane. In one preferred embodiment, the biocomposite membrane comprises two layers of cells, with each layer being cultivated on one surface of the biocomposite membrane and thereby forming an artificial skin that comprises living cells. A first layer of cells may be cultivated on one side of the biocomposite membrane, followed by cultivation of a second layer of cells on the other side of the membrane in accordance with the method described in Example 2. Techniques for isolating and/or cultivating cells are well known in the art. The selection of cells that are suitable for cultivating on the surfaces of the biocomposite membrane include, but are not limited to, fibroblasts, keratinocytes, melanocytes, cells originated from hair follicle and/or sweat gland, endothelial cells originated from the blood, blood cells, chondrocytes, osteocytes, osteoblasts and stem cells originated from the cord blood and/or bone marrow. The cells may be primary isolated cells or immortal cells, which are normal, genetically modified and/or malignant. In one preferred example, the biocomposite membrane prepared in accordance with the method of this invention was placed onto a sterilized filter holder within a co-culture device, keratinocytes were seeded onto one side of the biocomposite membrane, and cultivated until the cells reached confluence; then the biocomposite membrane was flipped over and fibroblasts were seeded onto the other side of the membrane, and cultivated for another 3 days to allow for cell attachment and growth. The co-cultured membrane was then flipped over again and lifted to the air-fluid level to allow for epidermal differentiation. Alternatively, the cultivation of fibroblasts may be performed before the cultivation of keratinocytes.

The in vitro cultivated biocomposite membrane comprising living cells on one or both of its two surfaces, i.e., the artificial skin, may be used either in vitro or in vivo, depends on the intended purposes. Since the cultivated artificial skin possesses a three dimensional structure that is similar to the real skin, hence it is suitable as a skin model for drug screening purposes such as determination of any drug toxicity and/or kinetics. The artificial skin may also be used in vivo, onto a living subject for repairing ear drum defect, and skin damages that include, but are not limited to, burn injuries, ulcers, impaired pigmentation, excisions or other dermatological conditions. The artificial skins thus prepared comprise living cells that are easily degraded, hence they need to be stored in an environment that may help prevent degradation and maintain cell growth for a period of at least 2 months in vitro. In one preferred embodiment, the in vitro cultivated artificial skin comprising a layer of confluence and differentiated keratinocytes on one side of the biocomposite membrane and a layer of populated fibroblasts on the other side of the membrane, was engrafted onto a skin wound, surgically created on the back of a test animal, then the wound was left to heal by itself without application of any other conventional wound therapy. Complete wound healing with successful engrafting was observed in 7 to 9 days, and by 28 days the skin is as smooth as if it had never experienced a surgical grafting.

The following Examples are provided to illustrate certain aspects of the present invention and to aid those of skilled in the art in practicing this invention. These Examples are in no way to be considered to limit the scope of the invention in any manner.

EXAMPLES

Statistic analysis Data presented herein was analyzed using the ANOVA two-factor with replication test, and the variances are further investigated by using the Student Newman-Keuls test. The data are shown as "mean±SE (SE: standard error)" when sample numbers (n) are no less than three. The result is statistically significant when the P value is less than 0.05 ($P<0.05$).

Example 1

Preparation of Biocomposites 1.1 Preparation of Collagen:PCL Biocomposites

Films of 1:4, 1:8 and 1:20 (w/w) collagen:PCL biocomposites were prepared in accordance with the method described by Dai et al (Biomaterials 25 (2004) 4263-4271). Briefly, aliquots of collagen solution (0.25% (w/v) in 1% acetic acid) were added to 4 ml glass vials and frozen at ±20° C. for approximately 45-50 minutes. Then, samples were transferred to a freezer at −70° C. for 35 minutes. Finally, the frozen samples were placed in a freeze dryer (Edwards Modulyo®) at −44° C. under 42 mbar vacuum for 24 hours. Aliquots (0.5 ml) of 0.5%, 1%, 2.5% (w/v) PCL/dichloromethane (DCM) solution were added carefully to the freeze dried collagen mats to prepare 1:4, 1:8, 1:20 (w/w) collagen:PCL biocomposites, respectively. The vials were kept stopped for 30 minutes before removing the lids to allow solvent evaporation overnight.

1.2 Preparation of Gelatin:PCL Biocomposites

Films of 1:4, 1:8 and 1:20 (w/w) gelatin:PCL biocomposites were prepared in accordance with the method described in Example 1.1 except aliquots of gelatin (type B) solution (0.1% w/v) was used to replace the collagen solution.

1.3 Preparation of Gelatin/Collagen:PCL Biocomposites

Films of gelatin/collagen:PCL biocomposites were prepared in accordance with the method described in Example 1.1 except aliquots of gelatin/10% collagen solution or gelatin/25% collagen solution was used to replace the collagen solution, respectively. The gelatin/10% collagen solution or gelatin/25% collagen solution was prepared by dissolving 0.2% (w/v) gelatin 0.2 ml in double distilled water followed by mixing 0.25% (w/v) collagen 0.025 ml or 0.062 ml, respectively. Films of both 1:8 and 1:20 (w/w) of gelatin/10% collagen:PCL biocomposites and gelatin/25% collagen:PCL biocomposites were obtained, respectively.

1.4 Characterization of the Synthetic Biocomposites of Examples 1.1, 1.2 and 1.3

The synthetic biocomposites of Example 1.1, 1.2 and 1.3 were characterized by the following assays, including 1) BCA total protein assay, to determine amounts of collagen and/or gelatin being released from the biocomposite; 2) differential scanning calorimetry (DSC); 3) scanning electron microscopy (SEM); 4) cell growth on the biocomposite membranes; and 5) immuno-histochemistry.

1.4.1 BCA assay

BCA total protein assays (Sigma) were performed in accordance with the manufacturer's instructions to estimate the amounts of collagen and/or gelatin being released from the biocomposites of Example 1.1, 1.2 or 1.3. Briefly, individual samples of biocomposites of Example 1.1, 1.2 or 1.3 were added to 7 ml glass shell vials containing 1 ml PBS, and incubated at 37° C. in a water bath. The release media was replaced completely by fresh PBS periodically and analyzed for protein content (i.e., gelatin and/or collagen) using the BCA total protein assay. Calibration samples of protein solution were prepared fresh before use in the BCA assay. A collagen and/or gelatin stock solution of concentration 1 mg/ml was prepared in advance, and serial dilutions were carried out to result in calibration samples of various concentration. The BCA working reagent was prepared according to the manufacturer's manual. For the BCA assay, a 96-well plate was used, and 200 µg of the BCA working reagent were mixed with 25 µg of a protein sample in each well. The study samples and standards were arranged in triplicate. Test and calibration samples were then placed in a water bath at 37° C. for 40 minutes. The absorbance of the calibration samples measured at 562 nm was used to produce a calibration curve of collagen and/or gelatin concentration that was subsequently used to calculate the protein concentration of the test samples.

1.4.2 Differential Scanning Calorimetry (DSC)

The thermal characteristics of biocomposites of Example 1.1, 1.2 or 1.3 (2-10 mg) were recorded using a Perkin-Elmer Pyris Diamond differential scanning calorimeter. All the samples were lightly pressed into the bottom of the pan to ensure good thermal contact. Sealed DSC pans were used in the study. Triplicate samples were heated at a rate of 10° C./min from 10° C. to 100° C. Peak melting temperature (Tm) and heat of fusion data for the PCL component of the materials were determined using the software facility of the DSC.

The latter measurement was subsequently used to estimate the percentage crystallinity of PCL in the biocomposites from the reported heat of fusion of 139.5 J/g for fully crystalline PCL. Indium was used as a standard.

1.4.3 Scanning Electron Microscopy (SEM)

The scanning electron microscopy was used to evaluate the surface morphology of the biocomposites of Example 1.1, 1.2 or 1.3, as well as the condition of cell adhesion, growth and distribution on the surface of the biocomposite membranes.

Briefly, samples (with or without cells grown on the surface of the biocomposites of Example 1.1, 1.2 or 1.3) were attached to aluminum SEM stubs using carbon tabs (Agar Scientific). Specimens were sputter coated with gold prior to examination using a HITACHI® S-3000N Scanning Electron Microscope.

1.4.4 Cell Growth on the Biocomposites

Growth of PHEK on biocomposites of Example 1.1, 1.2 or 1.3 Primary human epidermal keratinocytes (PHEK) were isolated and primarily cultured from the donated human foreskin samples after the surgery of circumcision in the study. EpiLife® keratinocyte culture medium (obtained from Cascade Biologics®, Inc., USA) was used for keratinocyte culture. The methods for treatment of skin samples, cell expansion and cell counting are well known in the relevant art. Briefly, PHEK isolated from child foreskin (P4) were seeded on the top surface of biocomposites of Example 1.1, 1.2 or 1.3, and TCP (24-well tissue culture plastics) at a cell density of $1.7 \times 10^5$ cells per cm$^2$ for a time intervals up to 9 days. Trypsin-EDTA solution was used for cell detachment followed by cell counting at day 1, 3, 6 and 9 using a Weber's haemocytometer.

Growth of PHDF on biocomposite of Example 1.1, 1.2 or 1.3 Primary human dermal fibroblasts (PHDF) were also isolated and primarily cultured from the donated human foreskin samples after the surgery of circumcision in the study. The methods for treatment of sample, cell expansion and cell counting are well known in the relevant art. Briefly, PHDF isolated from adult foreskin (P3-4) were seeded on the top surface of biocomposites of Example 1.1, 1.2 or 1.3 and TCP (24-well tissue culture plastics) at a cell density of $2.0 \times 10^4$ cells per cm$^2$ for a time intervals up to 10 days. Trypsin-EDTA solution was used for cell detachment followed by cell counting at day 1, 4, 7 and 10 using a Weber's haemocytometer.

1.4.5 Immunohistochemistry

Immuno-staining of PHEK PHEKs derived from child foreskin (P4) were seeded on the top surface of biocomposites of Example 1.1, 1.2 or 1.3 (1:8 and 1:20) and TCP (24-well tissue culture plastics) at a cell density of $1.7 \times 10^5$ cells/cm$^2$ for a time intervals up to 9 days. The growth and distribution of PHEK on biocomposites (1:8 and 1:20) on days 1 and 6 at an initial cell seeding density of $1.7 \times 10^5$ cells/cm$^2$ were examined under fluorescent microscope by labeling with the (primary) monoclonal mouse anti-human involucrin antibody 1:200 (United States Biological, Inc.), and the (secondary) rhodamine-conjugated polyclonal goat anti-mouse IgG 1:100 (United States Biological, Inc.) respectively.

Immuno-staining of PHDF PHDFs derived from adult foreskin (P3) were seeded on the top surface of Example 1.1, 1.2 or 1.3 (1:8 and 1:20) and TCP (24-well tissue culture plastics) at a cell density of $2.0 \times 10^4$ cells/cm$^2$ for a time intervals up to 10 days. The growth and distribution of PHDF on biocomposites (1:8 and 1:20) on days 1, 7 and 10 at an initial cell seeding density of $2.0 \times 10^4$ cells/cm$^2$ were examined under fluorescent microscope by labeling with the (primary) monoclonal mouse anti-human a tubulin antibody 1:200 (Santa Cruz Biotechnology, Inc.), and the (secondary) fluorescein (FITC)-conjugated polyclonal goat anti-mouse IgG 1:100 (Jackson ImmunoResearch Laboratories, Inc., USA) respectively.

1.4.6 Results

Figure 1B:
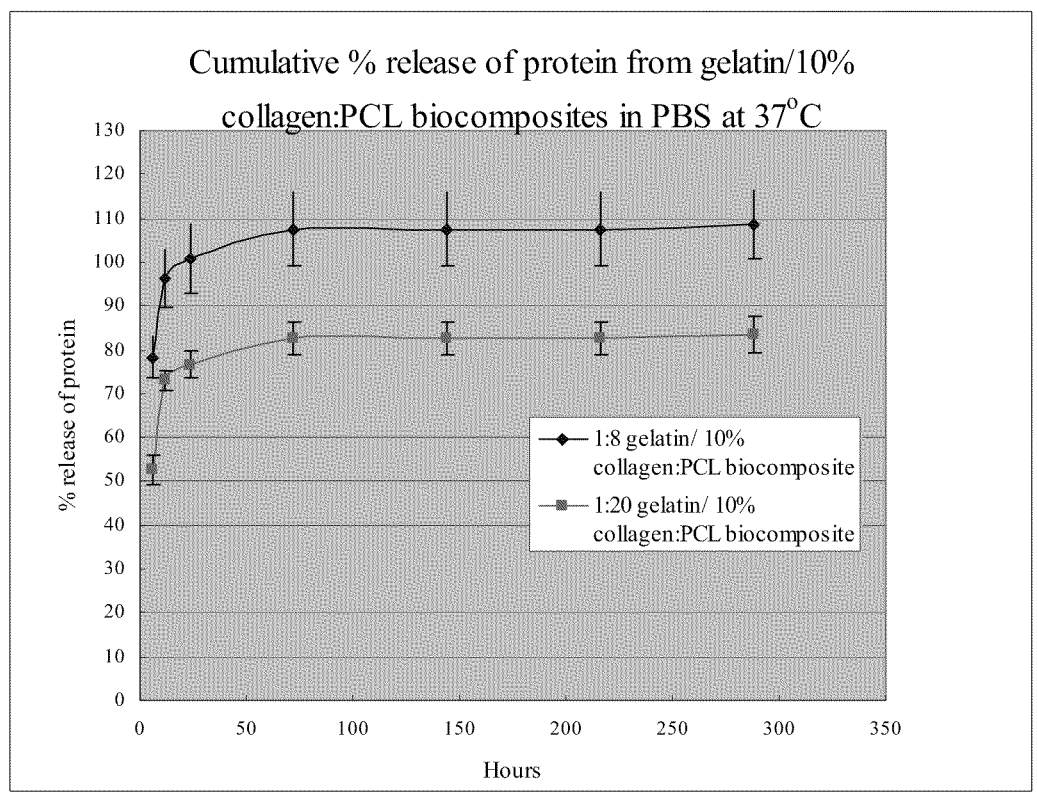

FIG. 1 illustrates an exemplified result of the amount of proteins (i.e., gelatin and/or gelatin/collagen) being released from the biocomposites of Examples 1.2 (FIG. 1A) and 1.3 (FIG. 1B). It was found that proteins, either gelatin or collagen, would rapidly release from the biocomposite membrane in the initial stage (i.e., within 24 hrs) and eventually reached a plateau after incubation for about 3 days. Moreover, it is evident that gelatin, being cheaper in terms of its cost and less susceptible to bacterial and enzymatic attack, is a good substituent for collagen and may form a biocomposite with PCL. DSC thermal analysis indicated that the melting points of the biocomposites of Examples 1.2 or 1.3 are similar to that of the PCL phase (Table 1).

Figure 2:
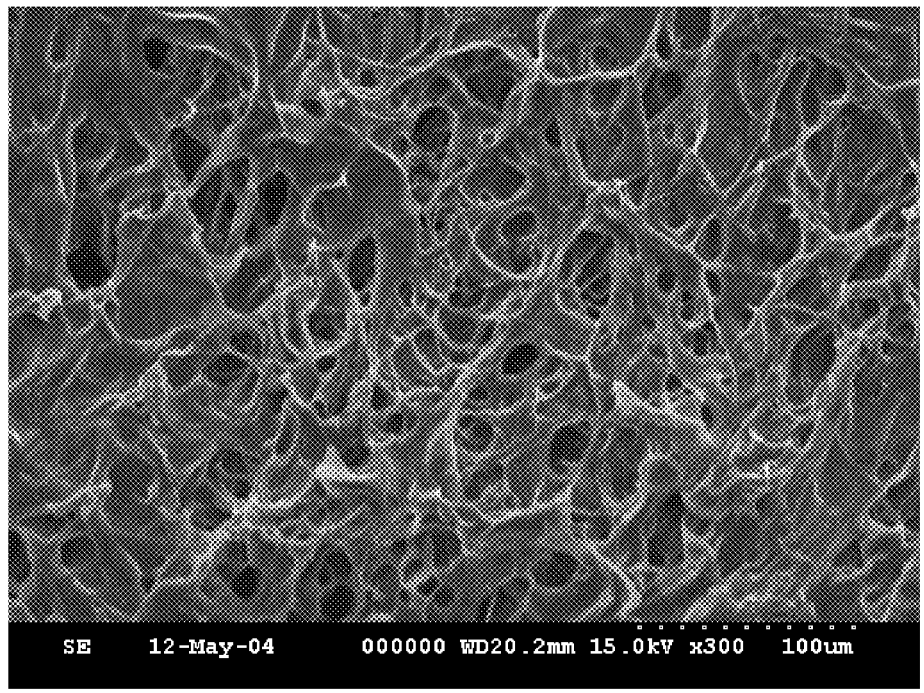
FIG. 2 are scanning electron microscopy (SEM) photographs of films of (A) 1:4 (w/w) gelatin:PCL, (B) 1:8 (w/w) gelatin:PCL, and (C) 1:20 (w/w) gelatin:PCL biocomposites of Example 1.2.
Figure 2B:
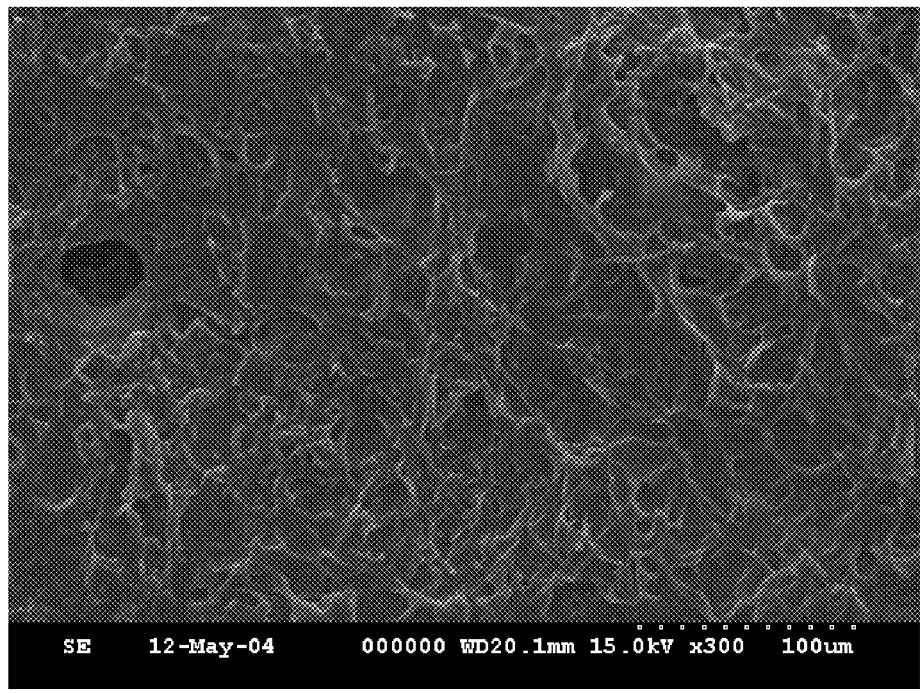
Figure 2C:
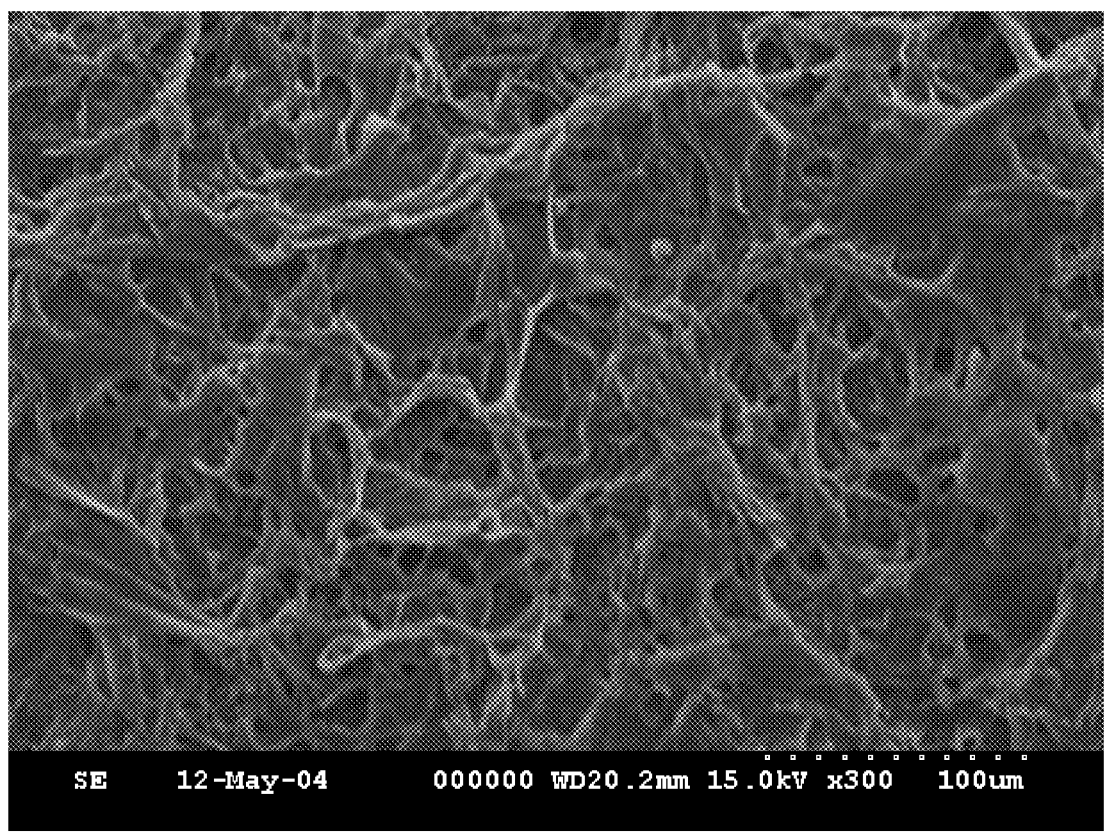
Figure 3A:
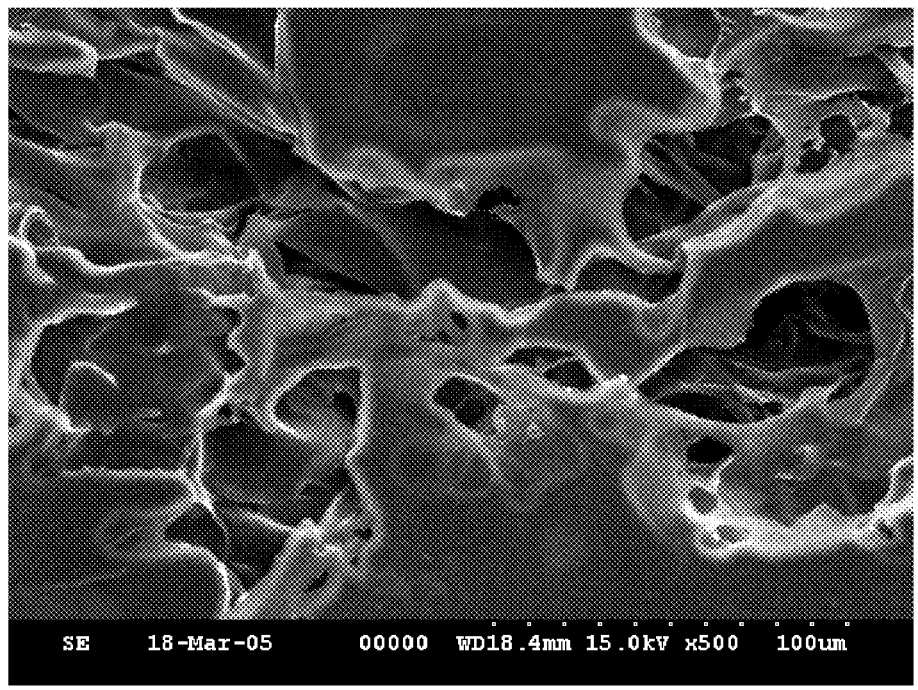
FIG. 3 are SEM photographs of films of (A) 1:8 (w/w) gelatin/10% collagen:PCL, (B) 1:20 (w/w) gelatin/10% collagen:PCL, (C) 1:8 (w/w) gelatin/25% collagen:PCL and (D) 1:20 (w/w) gelatin/25% collagen:PCL biocomposites of Example 1.3.
Figure 3B:
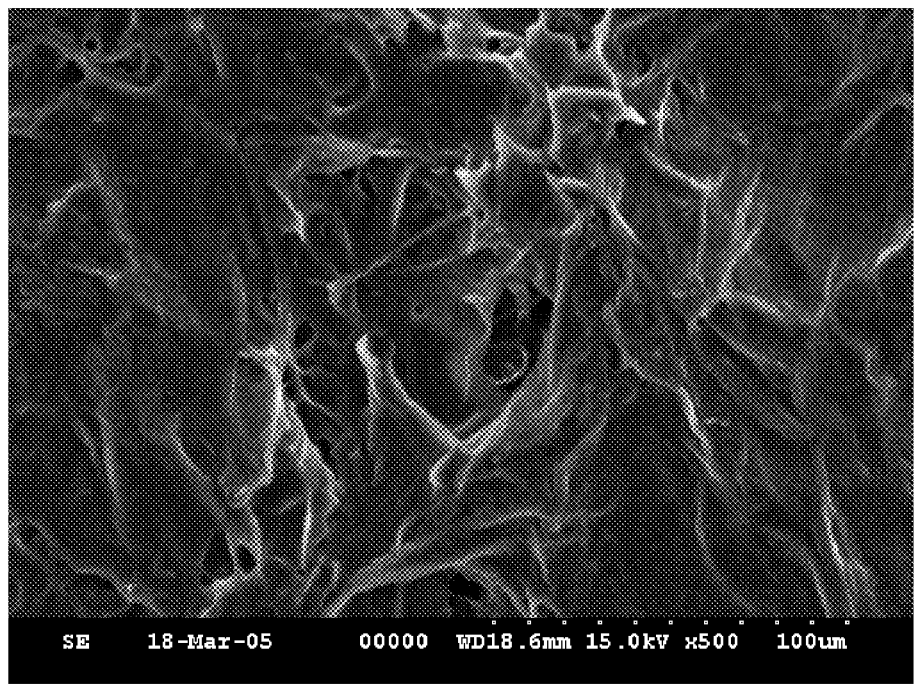
Figure 3C:
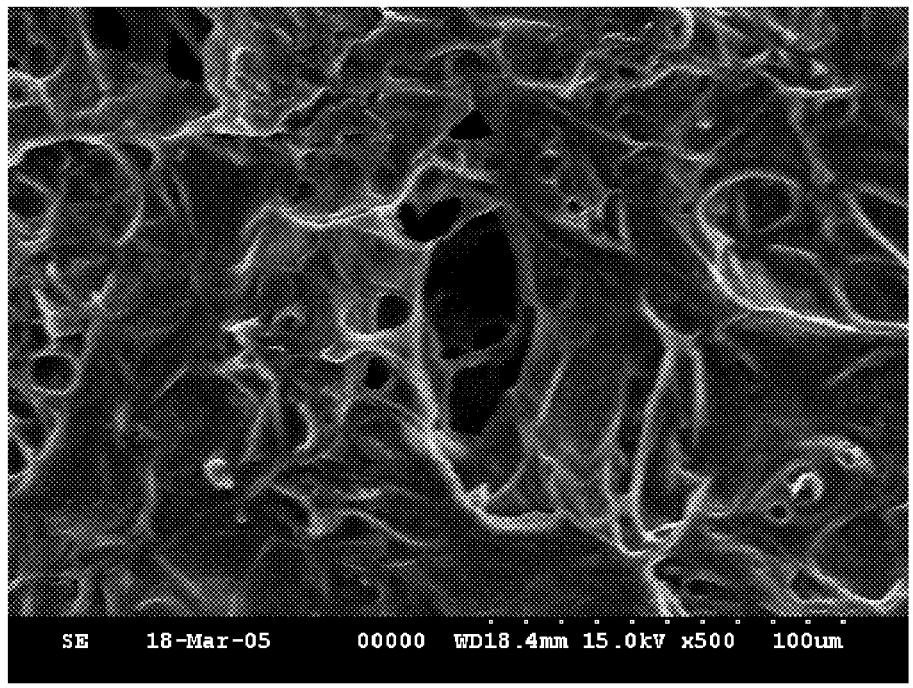
Figure 3D:
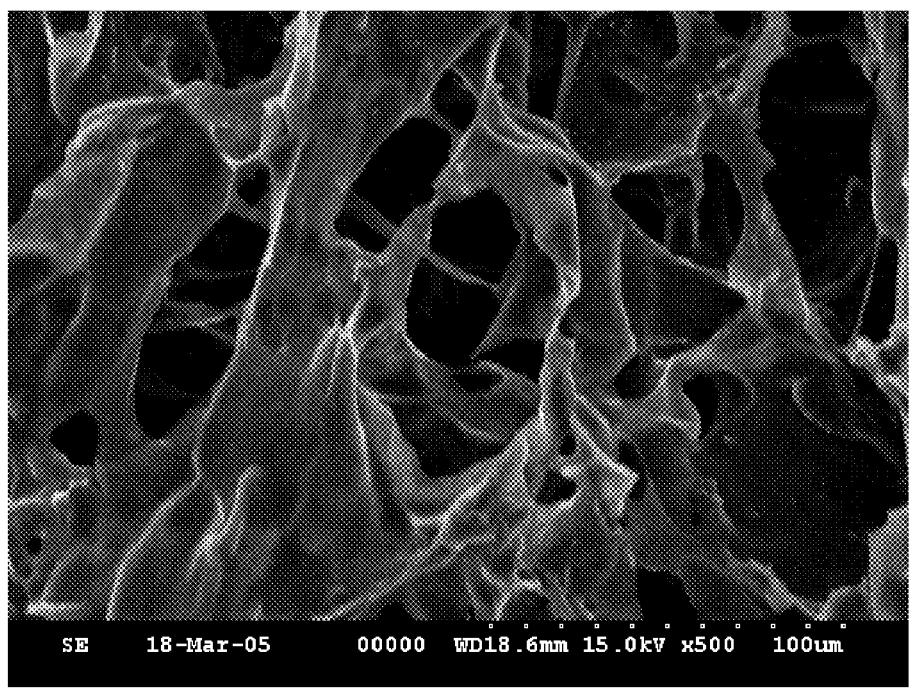
Figure 4A:
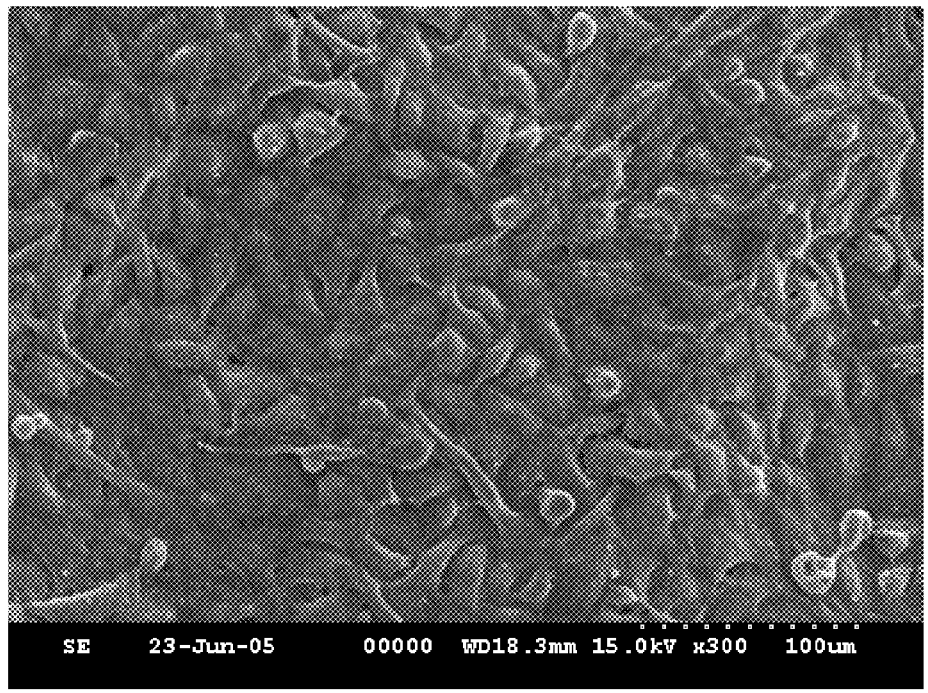
FIGS. 4A and 4B are SEM photographs for PHEK (primary human epidermal keratinocytes) grown on 1:8 gelatin:PCL biocomposite of Example 1.2 for 1 day and 3 days, respectively.
Figure 4B:
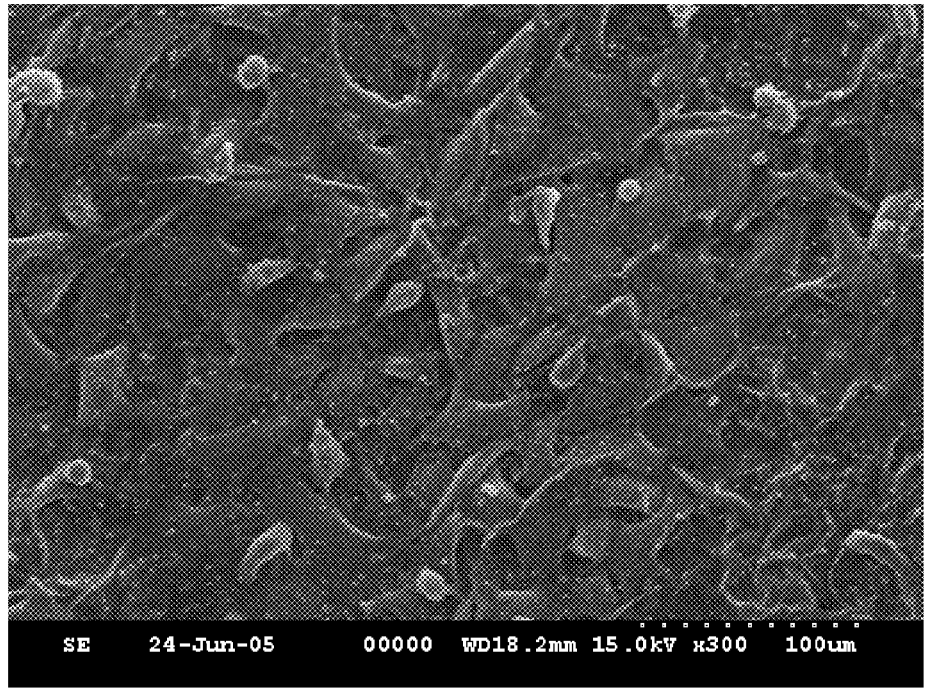
Figure 4C:
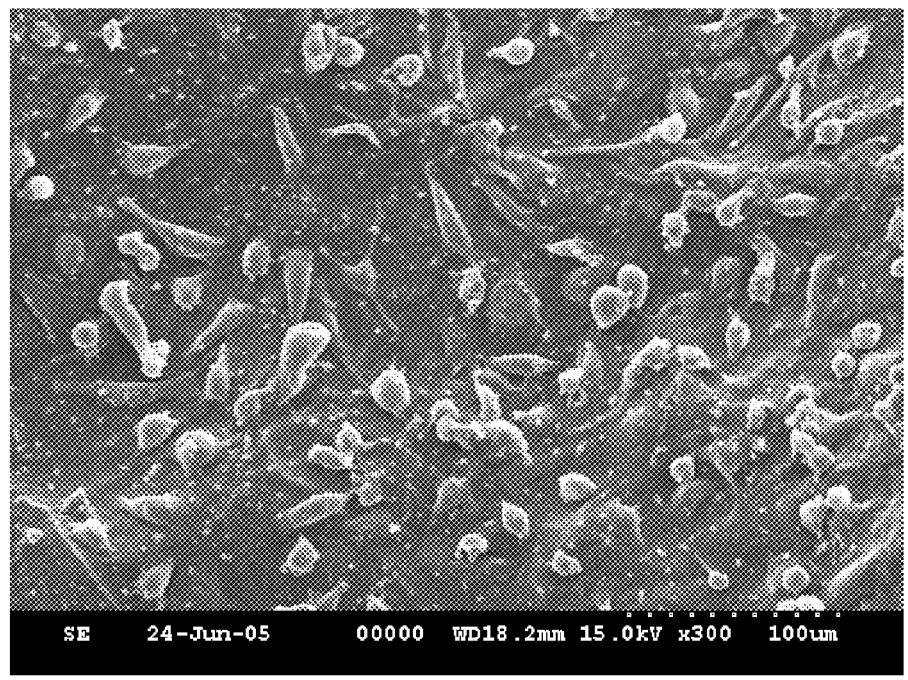
FIGS. 4C and 4D are SEM photographs for PHEK grown on 1:20 gelatin:PCL biocomposite of Example 1.2 for 1 day and 3 days, respectively.
Figure 4D:
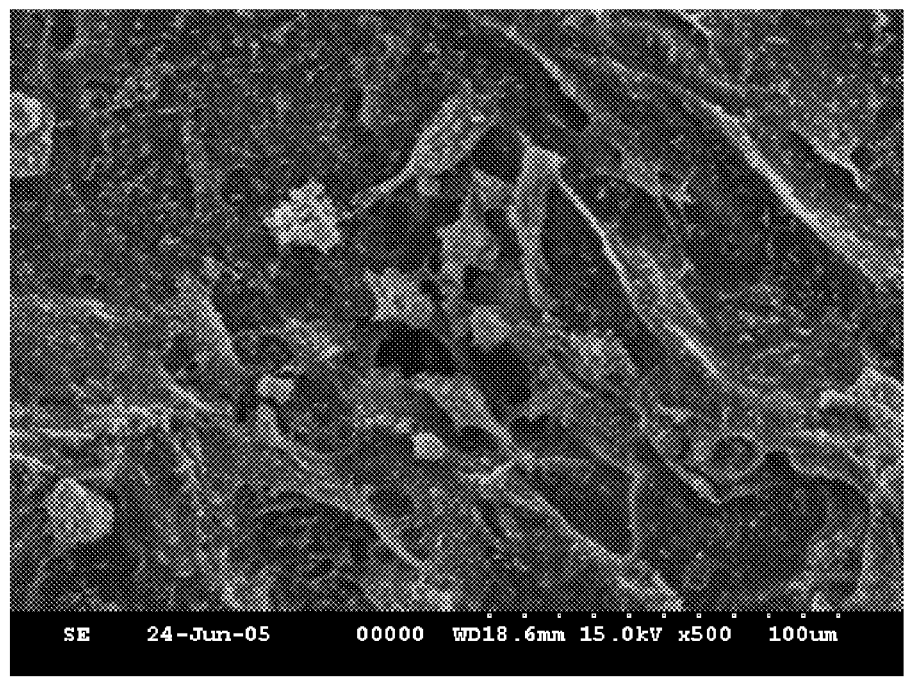
Figure 5A:
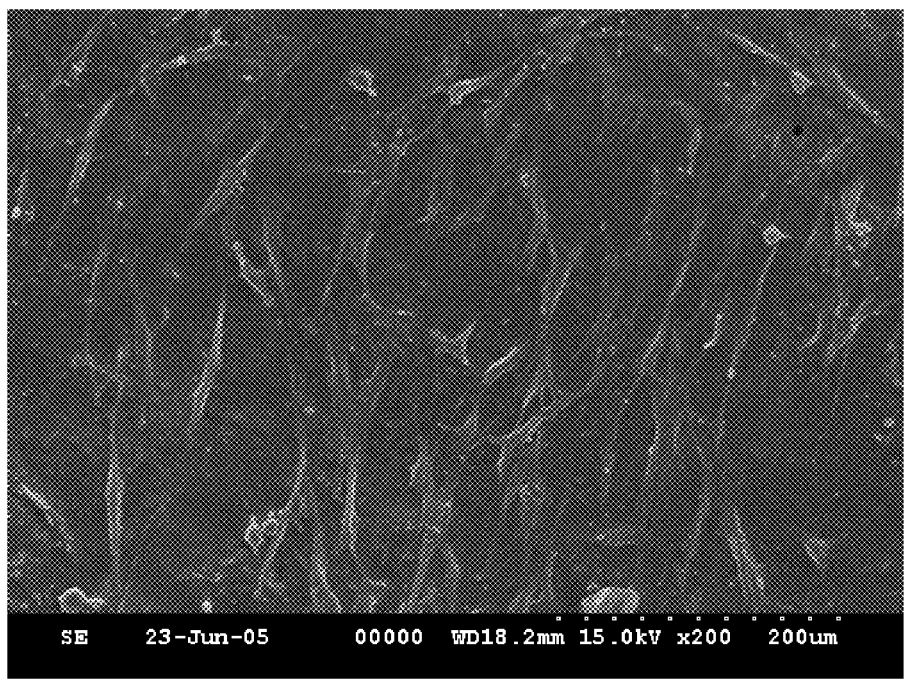
FIGS. 5A and 5B are SEM photographs for PHDF (primary human dermal fibroblasts) grown on 1:8 gelatin:PCL biocomposite of Example 1.2 for 1 day and 4 days, respectively.
Figure 5B:
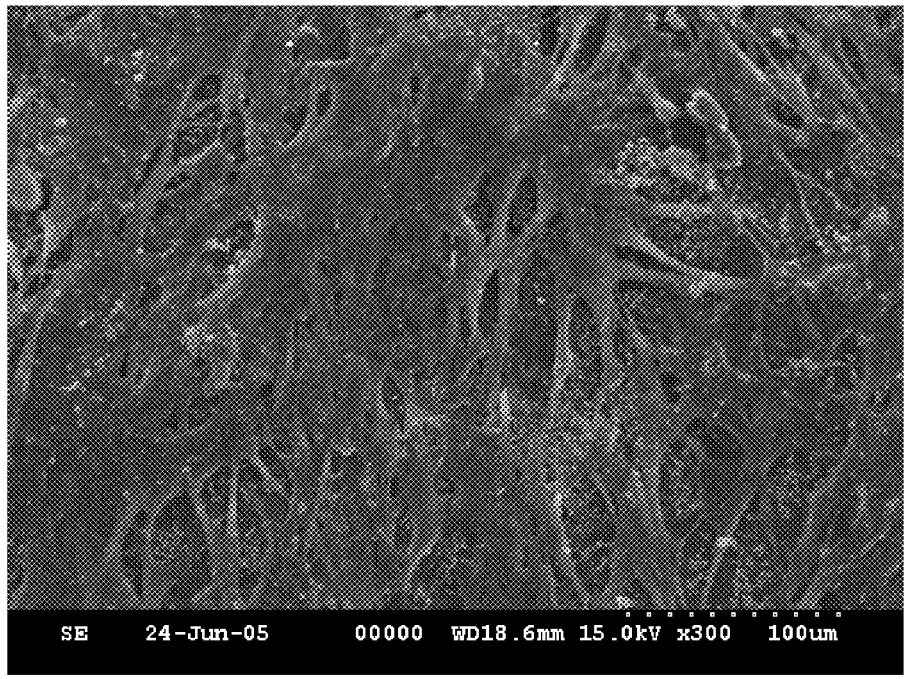
Figure 5C:
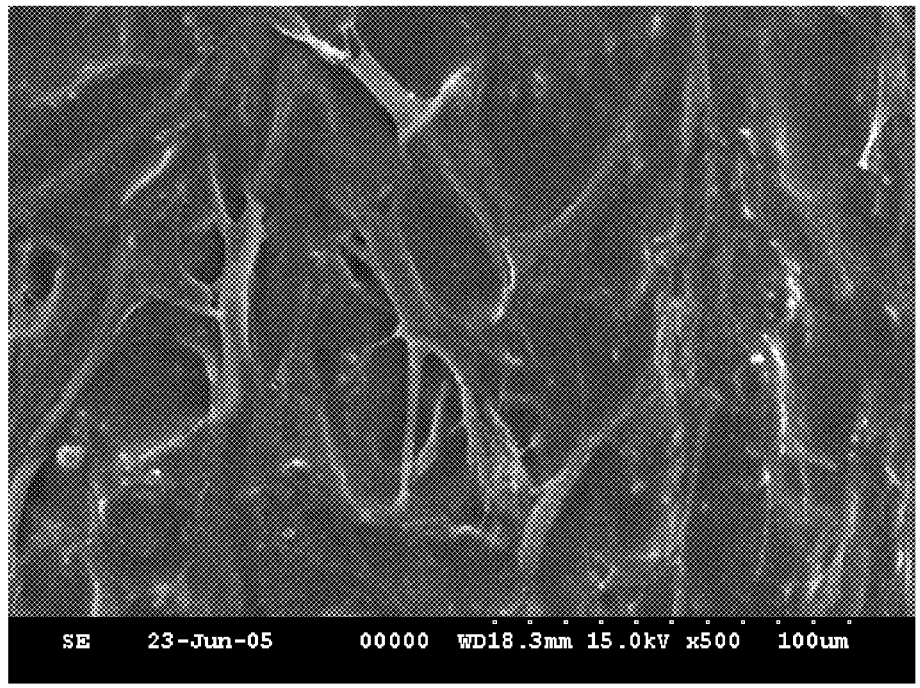
FIGS. 5C and 5D are SEM photographs for PHDF grown on 1:20 gelatin:PCL biocomposite of Example 1.2 for 1 day and 4 days, respectively.
Figure 5D:
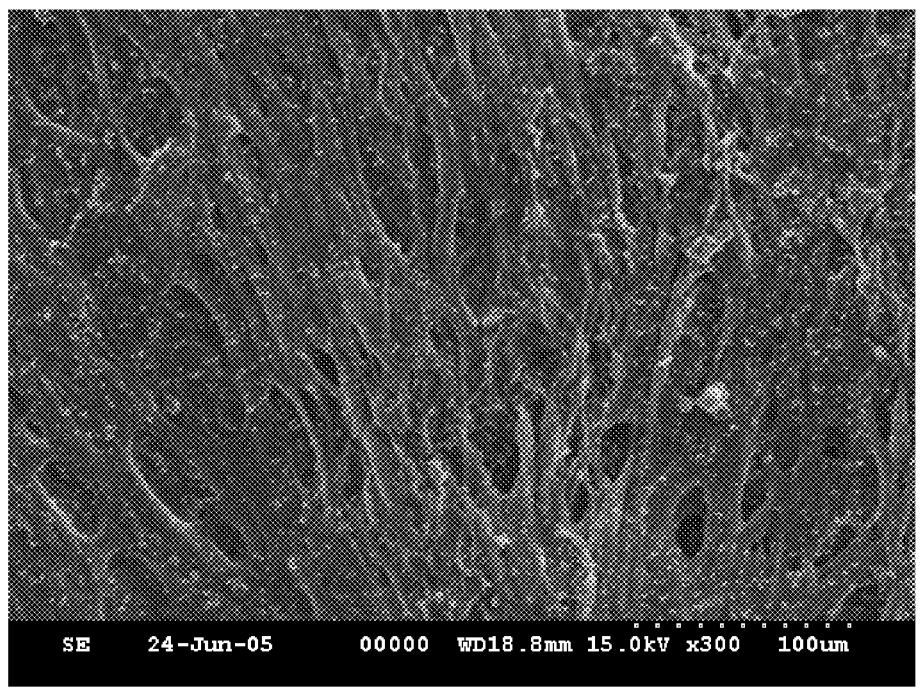
Figure 6A:
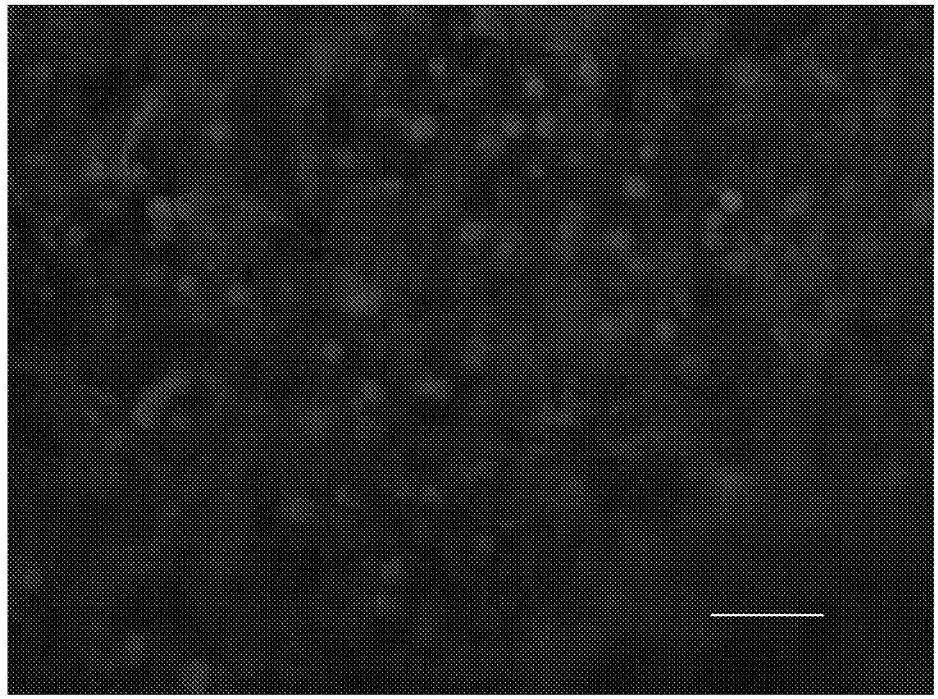
FIGS. 6A and 6B are immunostaining photographs for PHEK grown on 1:8 or 1:20 gelatin:PCL biocomposite of Example 1.2 for 6 days, respectively (100×, scale bar:100 µm), in which the primary antibody used for labeling of involucrin was monoclonal mouse anti-human involucrin antibody 1:100, and the secondary antibody used was rhodamine-conjugated goat anti-mouse IgG 1:100.
Figure 6B:
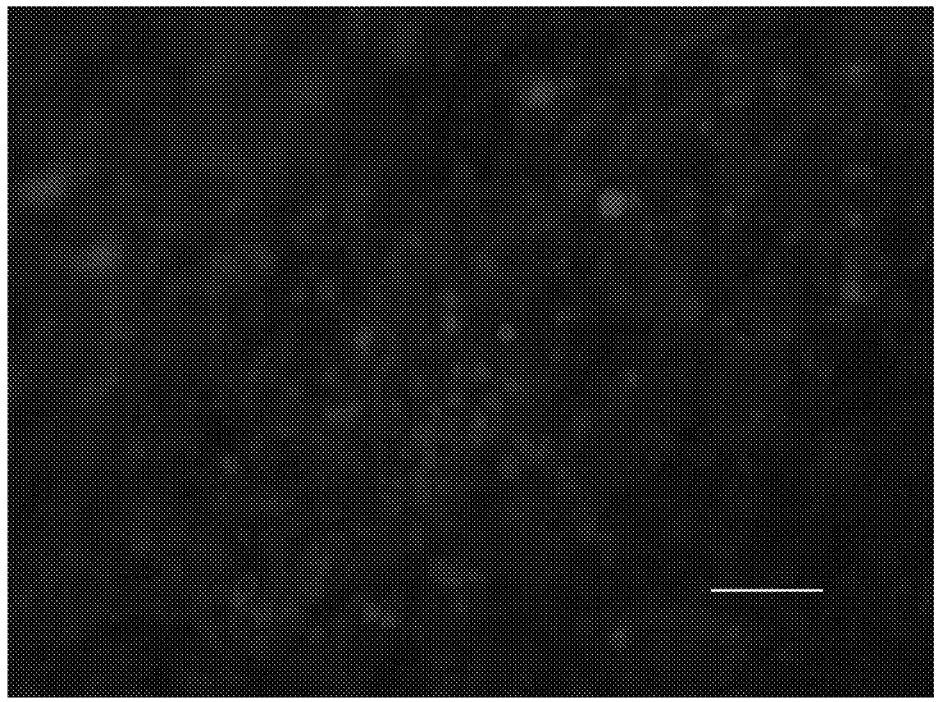
Figure 6C:
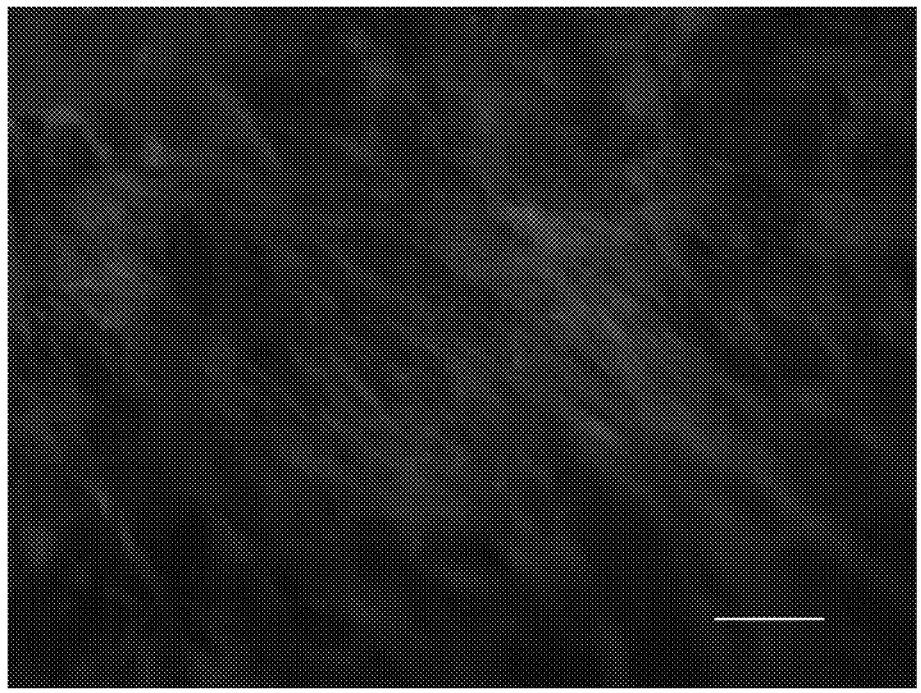
FIGS. 6C and 6D are immunostaining photographs for PHDF grown on 1:8 gelatin:PCL biocomposite of Example 1.2 for 7 days and 10 days, respectively (100×, scale bar:100 µm), in which the primary antibody used for labeling of α-tubulin was monoclonal mouse anti-human α-tubulin antibody 1:100, and the secondary antibody used was fluorescein (FITC)-conjugated goat anti-mouse IgG 1:100.
Figure 6D:
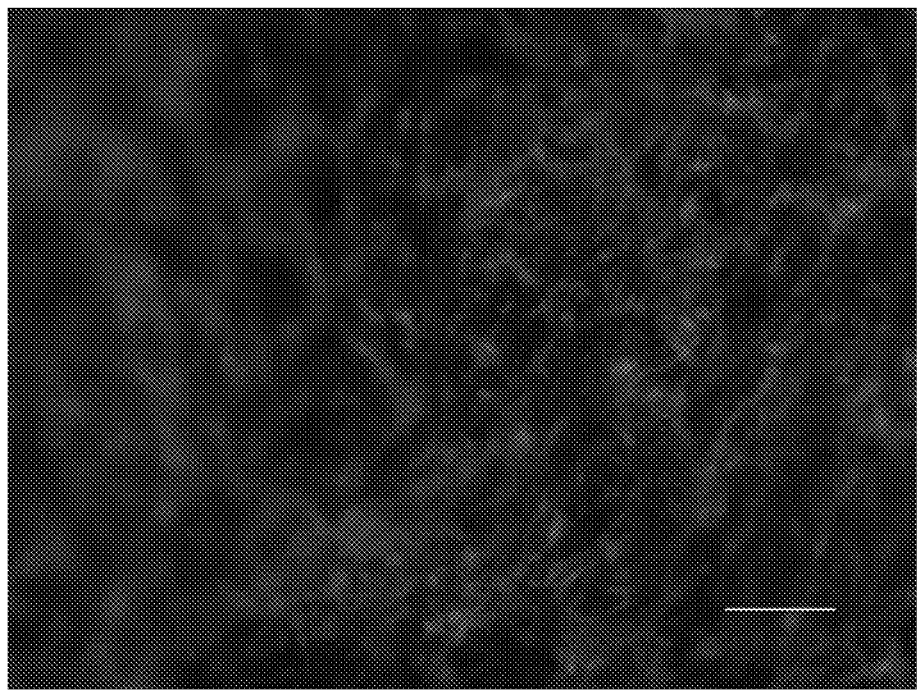
Figure 6E:
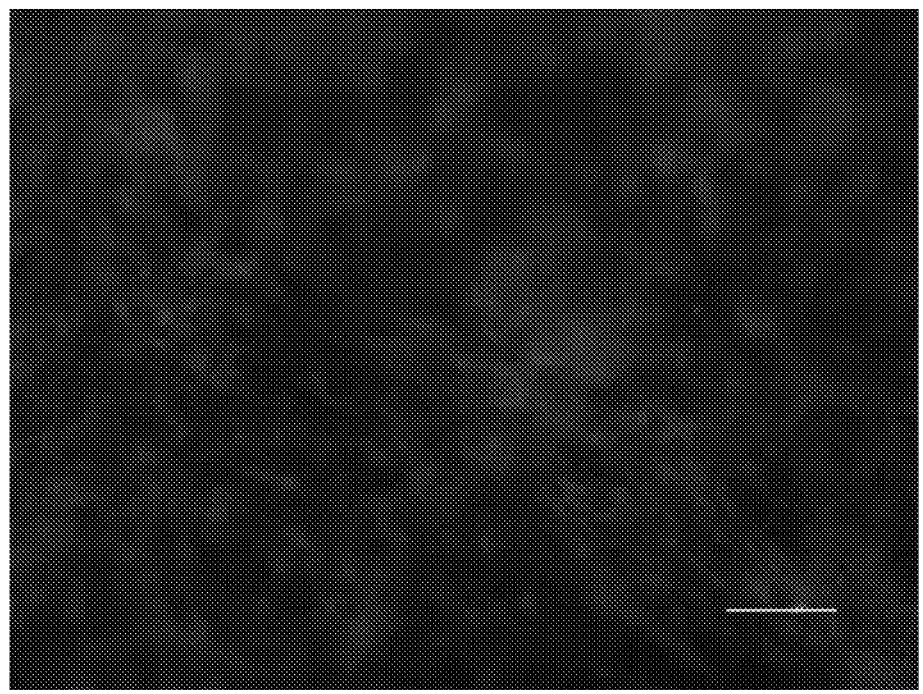
FIGS. 6E and 6F are immunostaining photographs for PHDF grown on 1:20 gelatin:PCL biocomposite of Example 1.2 for 7 days and 10 days, respectively (100×, scale bar:100 µm), in which the primary antibody used for labeling α-tubulin was monoclonal mouse anti-human α-tubulin antibody 1:100, and the secondary antibody used was fluorescein (FITC)-conjugated goat anti-mouse IgG 1:100.
Figure 6F:
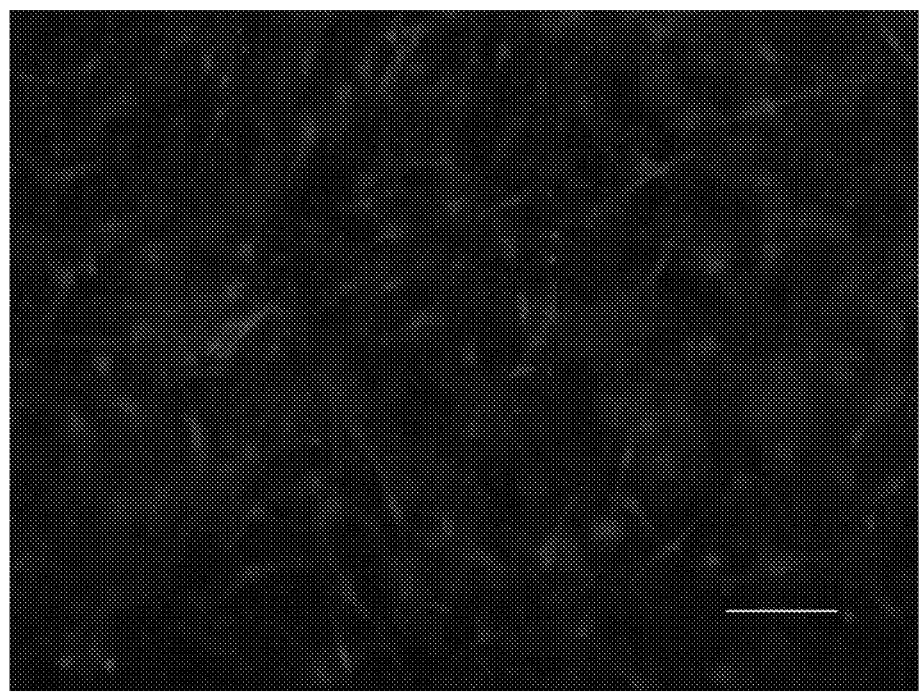
Figure 7:
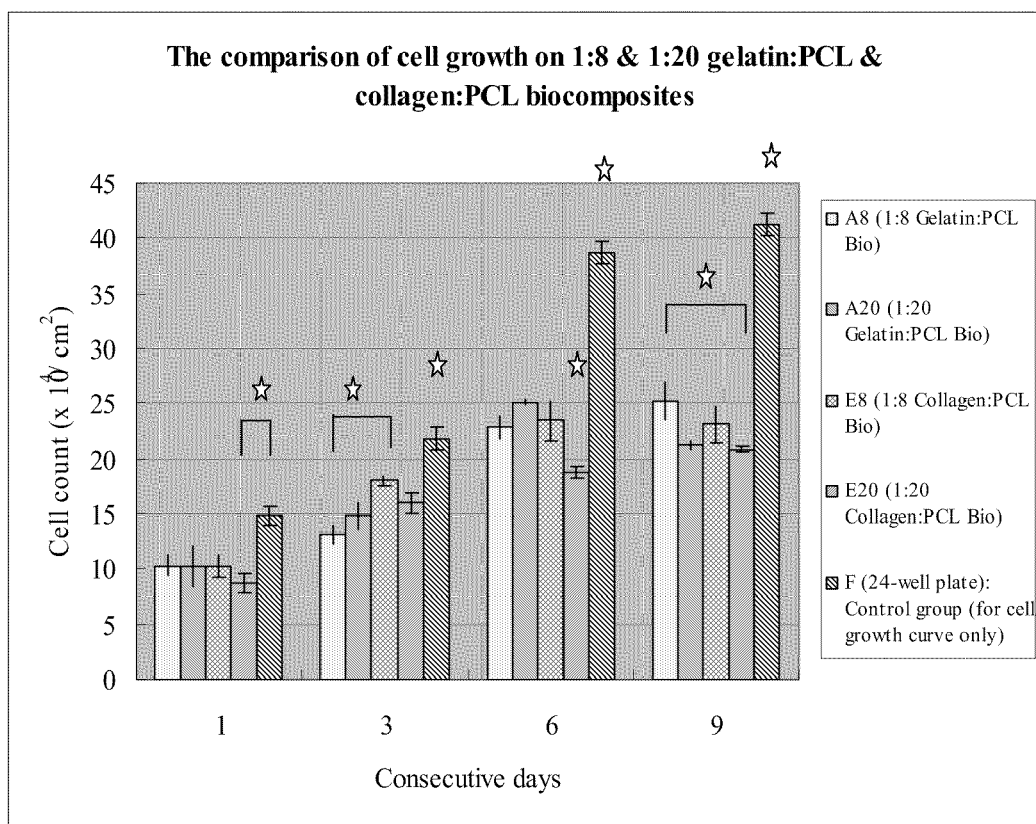
FIG. 7 illustrates the comparison of PHEK growth on biocomposites of gelatin:PCL (Example 1.2) and collagen:PCL (Example 1.1) and TCP, cell confluence was observed in the TCP control group at day 9, and cell counting was performed at days 1, 3, 6 and 9 (n=4±SE; ANOVA: P<0.05; Newman-Keuls: *P<0.05)
Figure 8:
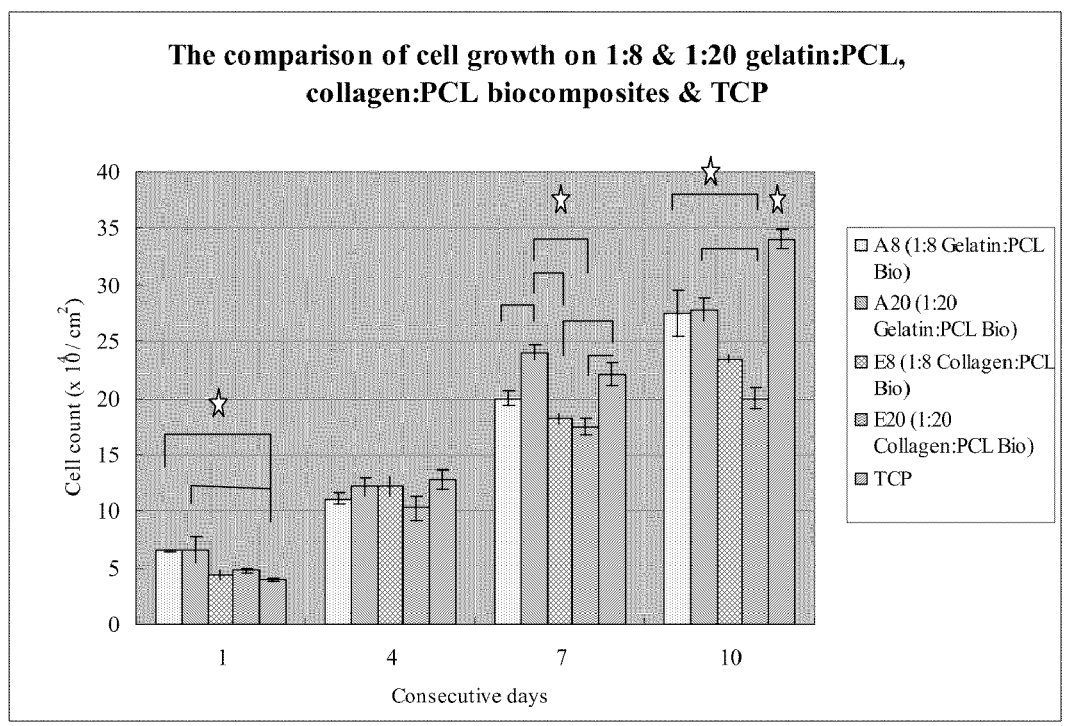
FIG. 8 illustrates the comparison of PHDF growth on biocomposites of gelatin:PCL (Example 1.2) and collagen:PCL (Example 1.1) and TCP, submerged growth of PHDF was allowed for 10 days, and cell counting was performed at days 1, 4, 7 and 10 (n=4±SE; ANOVA: P<0.05 except p=0.344 at day 4; Newman-Keuls: *P<0.05 except at day 4)
Figure 9:
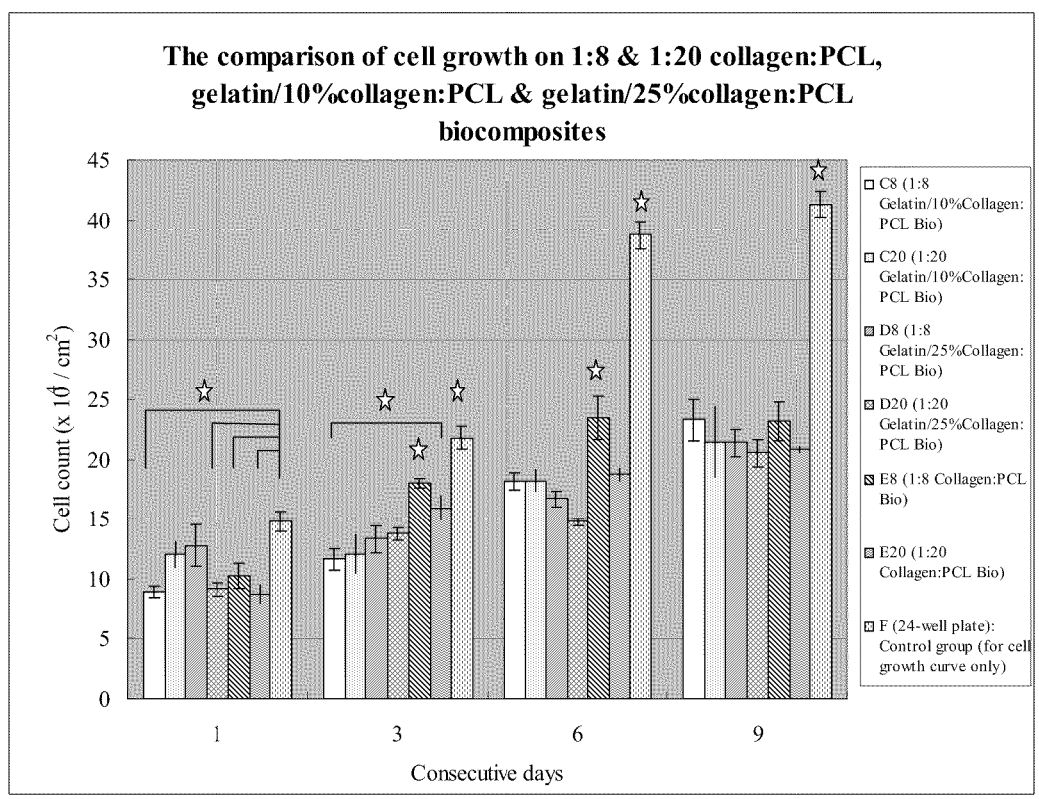
FIG. 9 illustrates the comparison of PHEK growth on biocomposites of gelatin/10% collagen:PCL and gelatin/25% collagen:PCL (Example 1.3) and TCP, submerged growth of PHEK was allowed for 10 days, cell confluence was observed in the TCP control group at day 9, and cell counting was performed at days 1, 3, 6 and 9 (n=4±SE; ANOVA: P<0.05; Newman-Keuls: *P<0.05)
Figure 10:
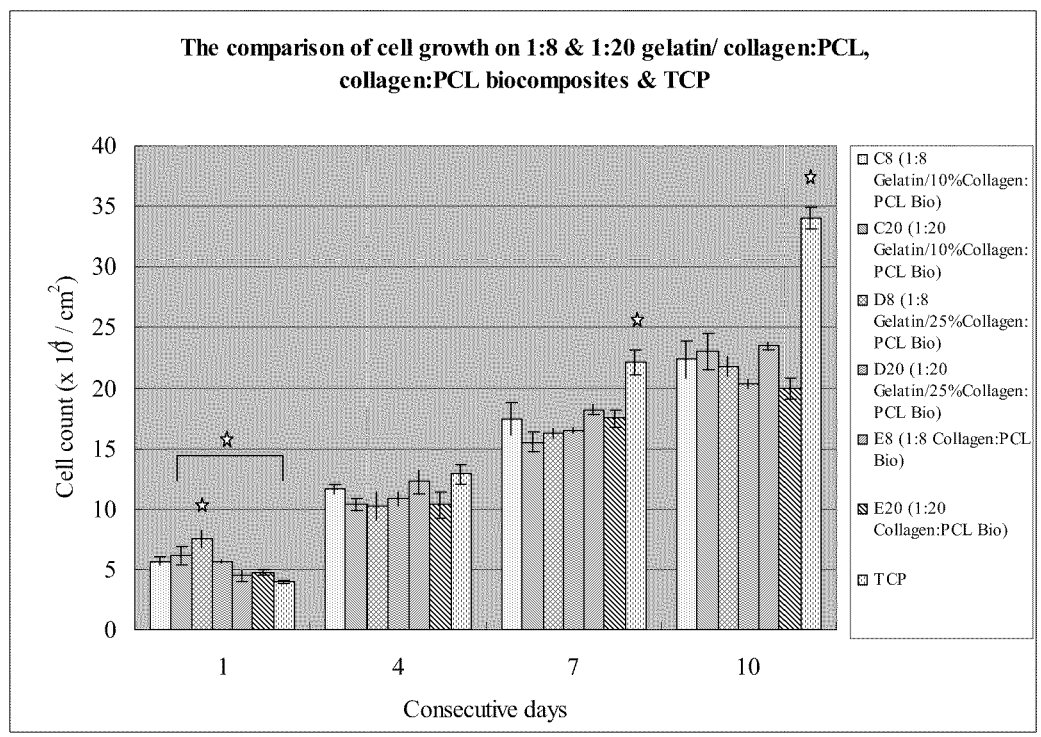
FIG. 10 illustrates the comparison of PHDF growth on biocomposites of gelatin/10% collagen:PCL and gelatin/25% collagen:PCL (Example 1.3) and TCP, submerged growth of PHDF was allowed for 10 days, and cell counting was performed at days 1, 4, 7 and 10 (n=4±SE; ANOVA: P<0.05 except p=0.344 at day 4; Newman-Keuls: *P<0.05 except at day 4)

The morphology of the synthetic biocomposites with or without cells grown on their surfaces was investigated by use of both SEM and immunohistochemistry. SEM photographs reveal an irregular pore and fibrous structure of the synthetic biocomposites per se, which is suitable as a scaffold for cells to grow on (FIGS. 2 and 3). The growth of cells (PHEK or PHDF) on any of the biocomposites prepared in accordance with the method described above were further confirmed by SEM (FIGS. 4 and 5), immuno-staining (FIG. 6) and by counting the cell numbers on the synthetic membrane surfaces (FIGS. 7, 8, 9 and 10). The comparison of the growth of PHEK on the biocomposites of Example 1.1 and 1.2 are illustrated in FIG. 7, whereas the comparison of PHDF growth on the same membranes is illustrated in FIG. 8. It is found that cell growth on gelatin:PCL biocomposites (Example 1.2) is at least as good as that on collagen:PCL biocomposites (Example 1.1), in some cases such as growth of PHEK on day 9 or growth of PHDF on day 10, cell growth on gelatin:PCL biocomposites (example 1.2) is even superior than that on collagen:PCL biocomposites (Example 1.1). Similar results are also observed for cell growth (PHEK or PHDF) on the biocomposites of Example 1.3. Results are illustrated in FIGS. 9 and 10.

TABLE 1

Thermal characteristics of Biocomposites of Example 1.2 and 1.3

| | Tm (□) | % crystallinity |
|---|---|---|
| Biocomposite of Example 1.2: gelatin:PCL (n = 3 ± SE) | | |
| Gelatin:PCL ratio (w/w) | | |
| PCL film | 62.8 ± 0.2 | 54.2 ± 5.4 |
| 1:4 | 60.2 ± 0.8 | 51.9 ± 2.7 |
| 1:8 | 59.8 ± 0.8 | 56.0 ± 1.6 |
| 1:20 | 62.4 ± 0.6 | 58.3 ± 0.5 |
| Biocomposite of Example 1.3: gelatin/10% collagen:PCL (n = 3 ± SE) | | |
| Collagen:PCL ratio (w/w) | | |
| PCL film | 62.8 ± 0.2 | 54.2 ± 5.4 |
| 1:8 | 59.2 ± 0.9 | 53.9 ± 1.1 |
| 1:20 | 61.5 ± 1.2 | 54.8 ± 1.4 |
| Biocomposite of Example 1.3: gelatin/25% collagen:PCL (n = 3 ± SE) | | |
| PCL film | 62.8 ± 0.2 | 54.2 ± 5.4 |
| 1:8 | 58.3 ± 0.1 | 55.1 ± 0.7 |
| 1:20 | 59.8 ± 0.2 | 57.1 ± 0.8 |

Example 2

Preparation of Artificial Skins 2.1 Preparation of Artificial Skins by Co-Culturing Keratinocytes and Fibroblasts on the Biocomposites of Example 1

Artificial skins were prepared by co-culturing keratinocytes and fibroblasts on either side of the biocomposite membranes prepared in accordance with the method of Example 1. Briefly, a co-culture device having a sterilized filter holder (Swinnex) with a diameter of 13 mm was used to hold a UV-sterilized biocomposite membrane between its two open chambers, which allowed the cell culture medium to contact both sides of the membrane. PHEK ($1.7 \times 10^5$ cells/$cm^2$; child foreskin) at passage 4 were seeded on one side of the biocomposite film for about 6 days to achieve 80% to 90% confluence compared to the control group of growing PHEK with the same seeding density on polystyrene in 24-well tissue culture plastics (TCP). Biocomposite film containing sub-confluent keratinocytes were then turned upside down and transferred to the co-culture device. PHDF ($2 \times 10^4$ cells/$cm^2$; child foreskin) at passage 4 were seeded onto the other side (top surface) of biocomposite film for another 3 days (to achieve 100% confluence in keratinocyte culture on TCP). Finally, biocomposite membrane was turned upside down again and kept in submerged culture for another 6 days, and then lift onto the air-fluid level for another 10 days to enable keratinocyte differentiation.

Figure 11:
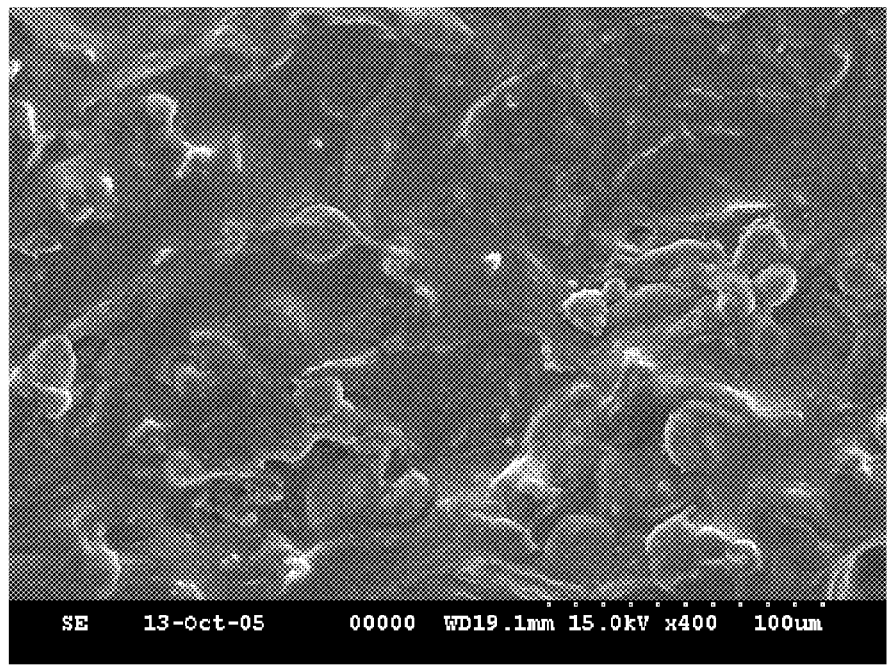
FIG. 11 is the SEM photograph of a confluent PHEK grown on an upper surface of 1:20 (w/w) collagen:PCL biocomposite (Example 1.1) for 35 days.
Figure 12:
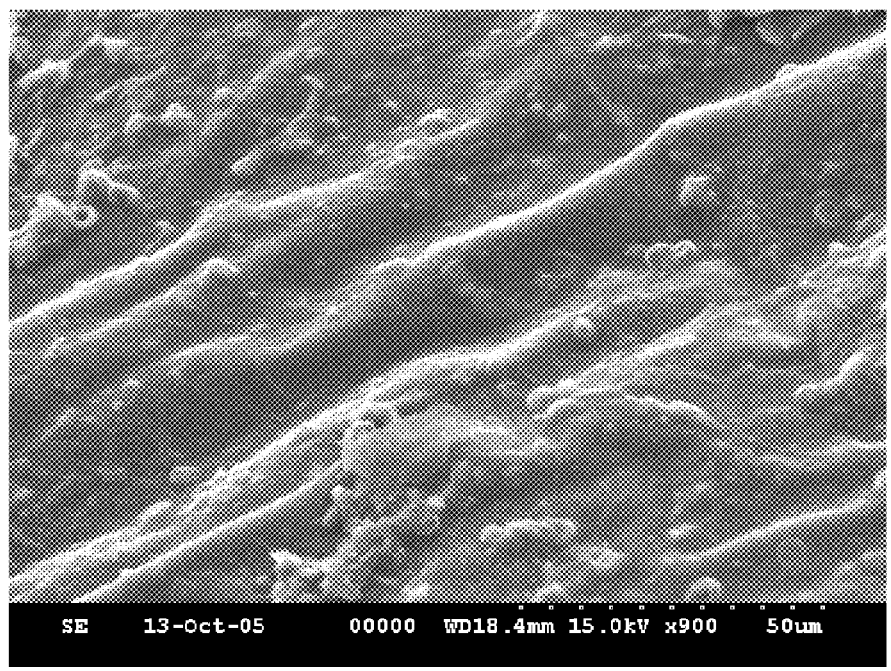
FIG. 12 is the SEM photograph of a confluent PHDF grown on the lower surface of the biocomposite of FIG. 11 pre-covered with PHEK for 35 days.
Figure 13:
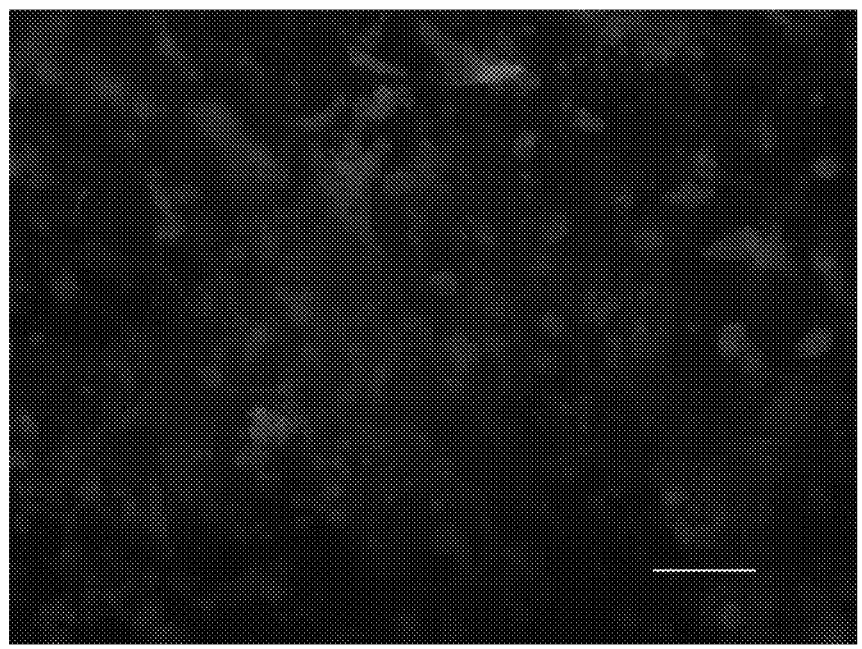
FIG. 13 is the immunostaining photograph of the PHEK grown on an upper surface of 1:20 (w/w) collagen:PCL biocomposite (Example 1.1) for 35 days (100×, scale bar: 100 µm)
Figure 14:
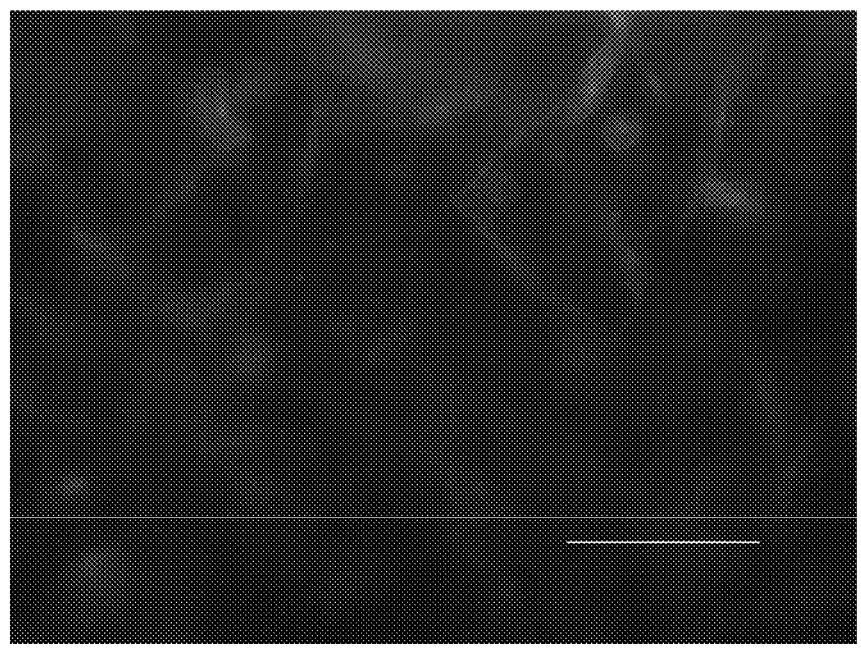
FIG. 14 is the immunostaining photograph of the PHDF grown on the lower surface of the biocomposite of FIG. 11 pre-covered with PHEK (100×, scale bar: 100 µm)

Cell cultures on either side of the membranes were monitored by SEM (FIGS. 11 and 12), or by immunohistochemistry using specific stains and antibodies against fibroblasts and keratinocytes (FIGS. 13 and 14). FIG. 11 is the SEM photograph of a layer of confluent and differentiated PHEK grown on an upper surface of the biocomposite of Example 1.1 for 35 days, with its immuno-staining photograph being shown in FIG. 13. FIG. 12 is the SEM photograph of a layer of populated PHDF grown on the lower surface of the PHEK-covered biocomposite of Example 1.1, also for 35 days, and its immuno-staining photograph is illustrated in FIG. 14. Similar results are expected for artificial skins prepared by using biocomposite of Example 1.2 or 1.3 as a scaffold to support cell growth.

2.2 Interaction of PHEK and PHDF in the Artificial Skin of Example 2.1

It is known that subepithelial fibroblasts in adult tissues, such as the oral mucosa and the skin, influence both normal epithelial growth and regeneration during wound healing by various secreted proteins/polypeptides such as keratinocyte growth factor (KGF) and hepatocyte growth factor. Therefore, to investigate the interaction between skin keratinocytes and fibroblasts in the co-cultured artificial skin of Example 2.1, keratinocyte growth factor (KGF) produced by fibroblasts populations after co-culture with keratinocytes and after stimulation with the pro-inflammatory cytokine IL-1β (10 ng/ml, R & D System, Oxford, UK) were measured.

The study and control groups were arranged as A to F groups: (A) Human fibroblast growth on TCP; (B) Human fibroblast growth on TCP with addition of IL-1β; (C) Human fibroblast growth on 1:20 (w/w) biocomposite of Example 1.1; (D) Human fibroblast growth on 1:20 (w/w) biocomposite of Example 1.1 with addition of IL-1β; (E) Human fibroblasts co-cultured with keratinocytes in the co-culture system, that is, artificial skin of Example 2; (F) Human fibroblasts co-cultured with keratinocytes in a co-culture system with addition of IL-1β.

The culture medium in each group was not changed during the experiment, and was collected after 24 and 48 hours, respectively and stored at −80° C. KGF proteins in the collected supernatants from the above study groups were determined by ELISA and the values compared.

KGF ELISA Human KGF sandwich ELISA was performed using standards and matched cytokine antibody pairs (R & D System) according to the manufacturer's protocol. These assays recognize both natural and recombinant KGF, with no significant cross-reactivity or influence with other cytokines, as described by the manufacturer. In brief, microtiter plates were coated with 5 μg/ml anti-KGF monoclonal antibody in PBS overnight and blocked with PBS containing 5% sucrose, 1% BSA and 0.05% $NaN_3$ for 1 hour. These and all other incubations were performed at room temperature. Between each of the described steps in the procedure the plates were washed three times with PBS (pH 7.4) containing 0.5% Tween 20. Standards and samples diluted in Tris-buffered saline (pH 7.3) containing 0.1% BSA and 0.05% Tween 20 were dispensed into each well and the plates were incubated for 2 hours. Biotinylated polyclonal goat anti-human antibody at a concentration of 50 μg/ml for KGF was added and the plates were incubated for 2 hours. Following incubation with Streptavidin HRP solution for 20 minutes the color reagent tetramethylbenzidine (TMB) was added for 30 minutes to develop a blue color. The reaction was stopped with 1 M $H_2SO_4$. Absorbance was read at 450 nm by an automatic plate reader with a reference wavelength of 570 nm.

Figure 15:
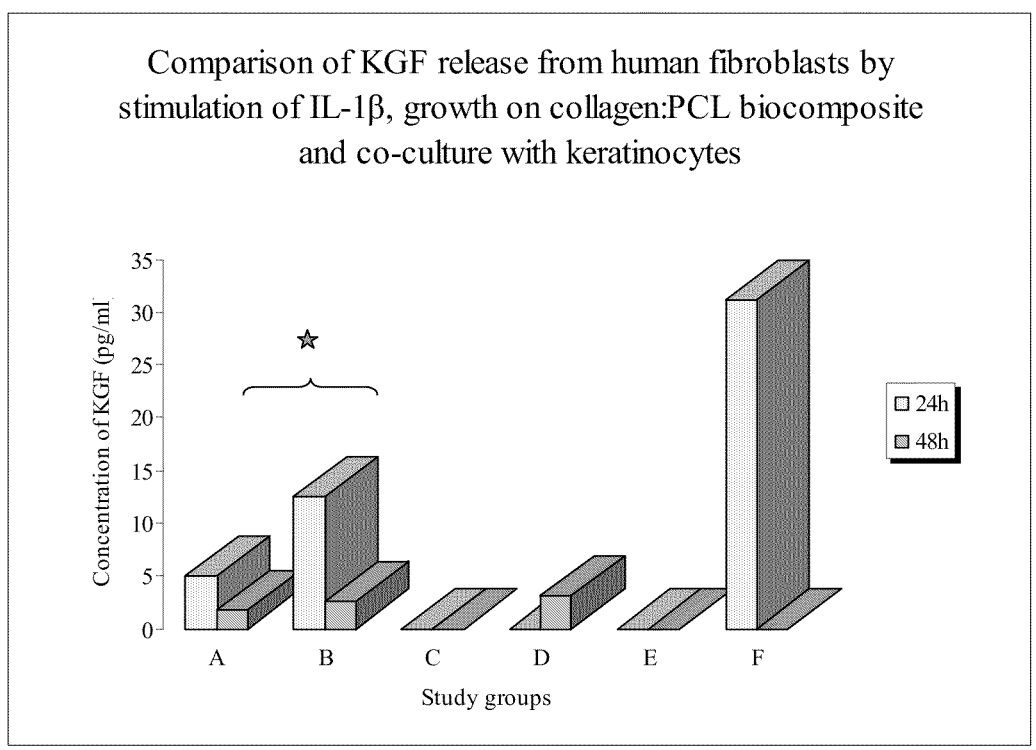
FIG. 15 illustrates the comparison of KGF release from human fibroblasts with (groups B, D and F) or without (groups A, C and E) stimulation of IL-1, human fibroblasts were culture on TCP (groups A and B), the biocomposite of Example 1.1 (groups C and D), and the biocomposite of Example 1.1 that were co-cultured with keratinocytes i.e., artificial skin of Example 2 (groups E and F) in accordance with a preferred embodiment of this invention.

Results FIG. 15 revealed that IL-1β may enhance the amount of KGF release by fibroblasts cultured on TCP (group B) significantly, when compared with that in cells without IL-1β stimulation (group A) at 24 hours (n=3±SE; P=0.01). However, no significant differences were measured in other paired study groups. The effect of cytokine IL-1β was proved to induce the production of KGF from PHDF grown on TCP at time interval of 24 hours in this study; however, the effect might be unapparent due to the change of cell-cell and/or cell-matrix interactions by co-culture of skin keratinocyte and fibroblast cells from a single donor, and therefore eliminating the pro-inflammatory cytokine stimulations, and/or the specific cell culture environment, i.e. the collagen:PCL biocomposite membrane.

Example 3

In Vivo Animal Study Using Artificial Skins of Example 2

3.1 In Vivo Animal Study

Athymic mice were used in this study. All animals were acquired, housed and studied in accordance with a protocol approved by the Institutional Animal Care and Use Committee of National Defense Medical Center, R.O.C.

The mice in this study were randomly divided into 3 groups, and surgical skin wounds (in round shape with 1.2 cm in diameter) were created to the depth of the panniculus carnosus on the flanks of the mice in each group. Then, an artificial skin of Example 2 (n=3), or a biocomposite of Example 1.1 (a blank biocomposite group, n=3) was grafted orthotopically to full-thickness of the skin wounds, respectively; whereas the skin wounds of the mice in the control group (n=3) were left without any graft treatment. Grafts (the artificial skin of Example 2, or the biocomposite of Example 1.1) were sewed attached with 4 stent-sutures around the wound margin, and then were covered with gel-type medium containing DMEM/gelatin/agarose/10% FCS covered with Tagaderm® transparent film, and finally sealed and fixed with elastic Omnifix® non-woven retention tapes (Hartmann Inc., Spain) to the surrounding murine skin. No gauzes were used as dressings and no post-operative treatments were given in this study. At 1 week after surgery, all dressings and sutures were removed, data were collected, and the healing wounds were left open to the air. The data of clinical evaluation of graft taking and surface area were collected by (1) photographing the wound area periodically at weekly intervals during the in vivo study periods; (2) clinical evaluation of the wound size and its appearance by the main investigator; and (3) histological analysis.

Figure 16:
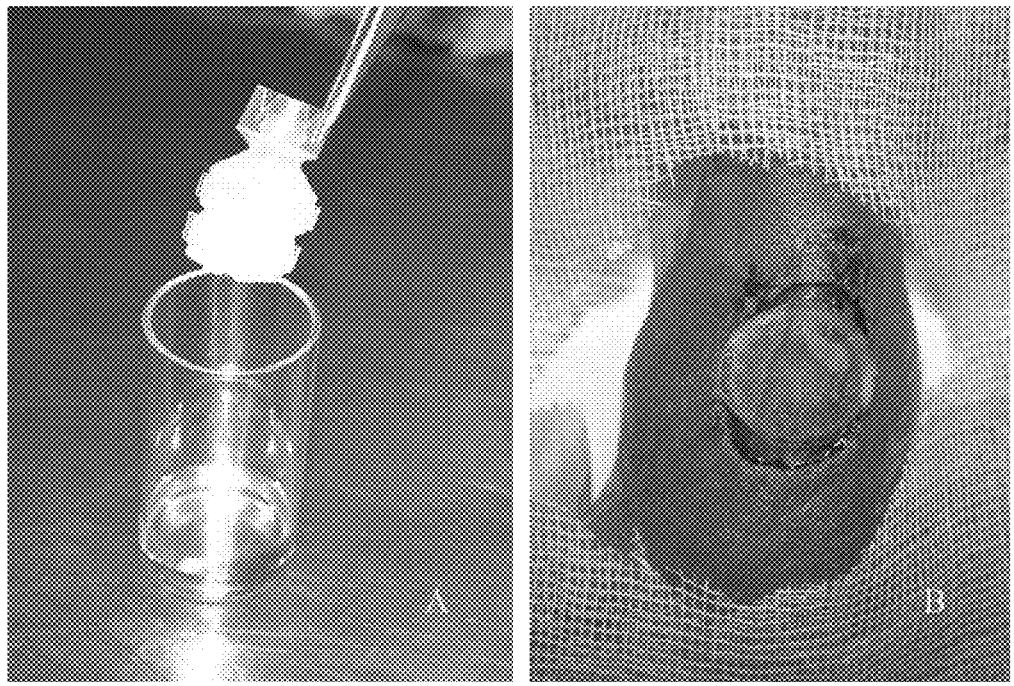
FIG. 16 illustrates the transplantation of artificial skin of Example 2 to the surgical wound on the back of an athymic mice, (A) the artificial skin based on 1:20 (w/w) collagen:PCL biocomposite in the co-culture device, and (B) the artificial skin being transferred to the skin wound.
Figure 17:
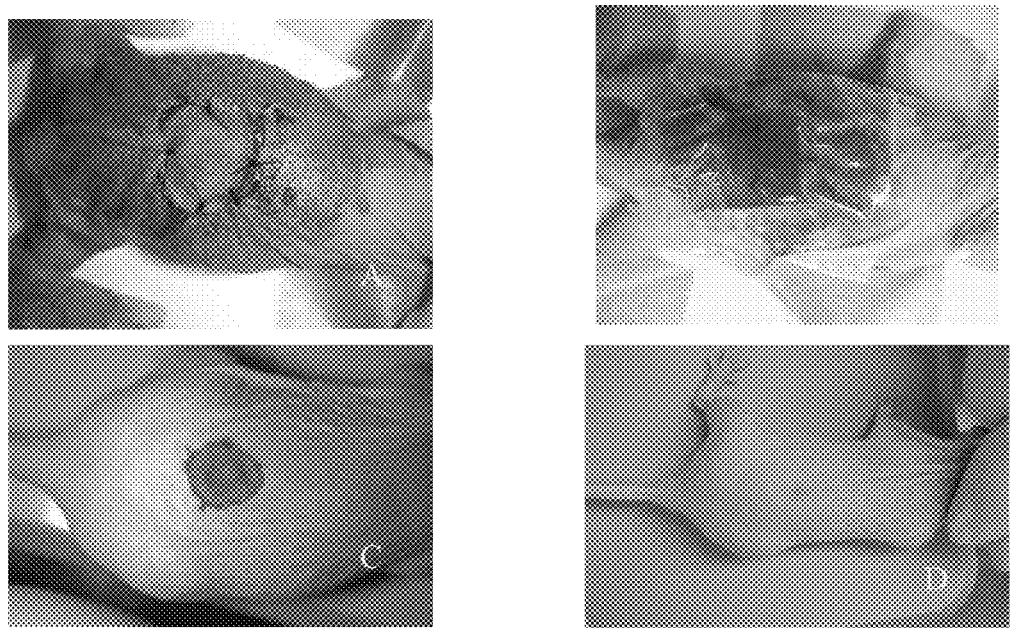
FIG. 17 are photographs taken at times when (A) an artificial skin of Example 2 was sewed attached on to the surgical wound with 4 stent-sutures around the wound margin; (B) the wound was subsequently covered with gel-type medium containing DMEM/gelatin/agarose/10% FCS covered with Tagaderm® transparent film on day 0, and (C) subsequently on day 7; and (D) day 28.

Photographs provided in FIG. 16 illustrate an exemplified transplantation of the artificial skin of Example 2 onto the surgical wound of an athymic mouse. Photographs in FIG. 17 were taken from the same mouse at the time when (A) the artificial skin of Example 2 was grafted onto the wound and sewed attached with sutures; (B) the wound was subsequently covered with gel-type medium on day 0; and subsequently on (C) day 7 and (D) day 28, respectively. Complete wound healing with successful engrafting was observed in 7 to 9 days, and by 28 days, the skin is as smooth as if it had never had a surgical wound.

Figure 18:
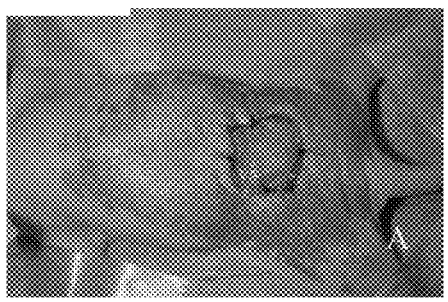
FIG. 18 are photographs taken at times when (A) a biocomposite of Example 1.1 was sewed attached onto the surgical wound of athymic mice with 4 stent-sutures around the wound margin on day 0, and subsequently on (B) day 7, (C) day 10 and (D) day 19.
Figure 18:
Figure 18:
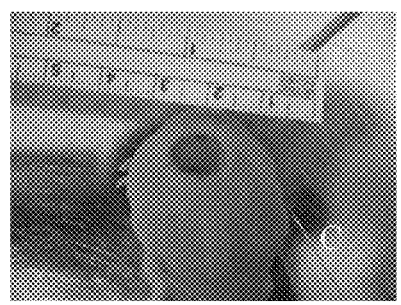
Figure 18:
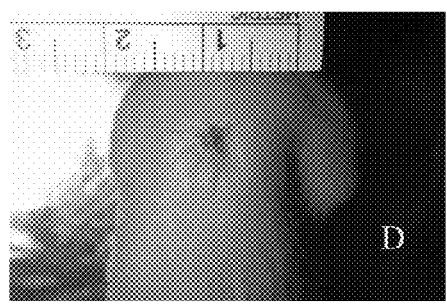
Figure 19:
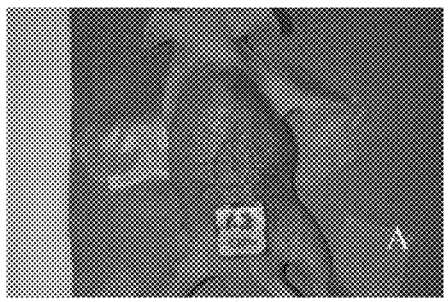
FIG. 19 are photographs taken at times when the surgical wound was left without any graft treatment on (A) day 0, (B) day 7, (C) day 10 and (D) day 19.
Figure 19:
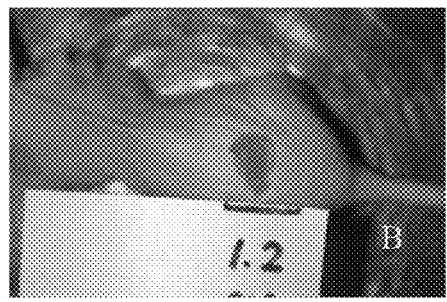
Figure 19:
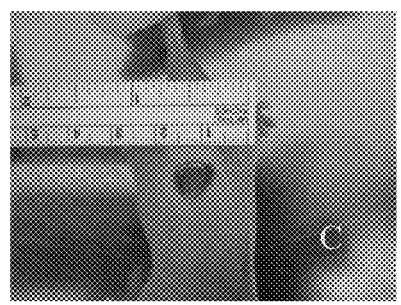
Figure 19:
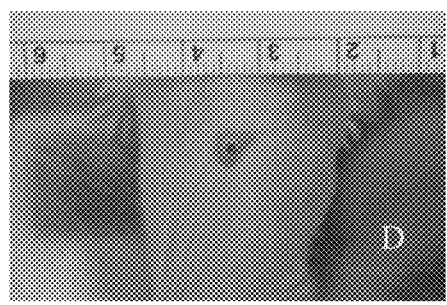

Photographs provided in FIGS. 18 and 19 illustrate the wound recovery on the mice treated with the biocomposite of Example 1.1 or without any graft treatment (the control group). It was noted that the wound in either the blank biocomposite group or in the control group was not completely healed by day 7; and spontaneous regeneration of skin followed by shrinkage of wound size was noted in the blank biocomposite group and retained open wound with almost complete wound closure at time intervals up to day 19 (FIG. 18, panel (D)).

3.2 Histological Study and Immunohistochemistry

The mice of Example 3.1 were sacrificed and the specimen including biocomposite and adjacent normal mouse tissue were widely excised for histological study based on both frozen and paraffin wax-embedded section methods by using H & E and Gomori's trichrome staining methods as well as immunohistochemical assay.

3.2.1 Immunohistochemical Staining

The growth and distribution of PHEK or PHDF on any the skin substitutes engrafted on the back skin of the athymic mice for a certain period of time were ascertained by immunohistochemistry assay. PHEK was labeled with monoclonal mouse anti-human involucrin antibody 1:200 (United States Biological, Inc.). The secondary antibody used for detection of involucrin was rhodamine-conjugated goat anti-mouse IgG 1:100 (United States Biological, Inc.).

Furthermore, PHEK and PHDF can also be labeled with monoclonal mouse anti-human D7-FIB antibody 1:200 (Novus® Biologicals, Inc.) that will not cross-reacted with mouse or rat, and the secondary antibody of rhodamine-conjugated goat anti-mouse IgG 1:100 (United States Biological, Inc.). Thus, the human-origin fibroblasts/epithelial cells are in red fluorescent staining alone in the artificial skin in vivo.

3.2.2 Histological Study with Paraffin Wax-Embedded Hematoxylin and Eosin-Y (H & E) Staining Method H & E staining with paraffin wax embedding procedure was used to distinguish the nuclei (blue-black) and cytoplasm (pink) in terms of the status of cell attachment, growth and distribution on the surface of the skin substitute engrafted on the back wound of any of the mice group of Example 3.1 in vivo.

Briefly, tissue samples of the mice were obtained and fixed in 10% formalin, then were embedded in wax and stored in the fridge at ±20☐. A slice machine (Microm® HM 400) was used to slice the samples in cross section with a thickness of 10 μm. The sample slices were then transferred to a flotation bath (Fisher® Tissue Prep™ Flotation Bath Model 134) at 30° C., then to water bath at 25° C. for cooling and subsequently onto glass slides. The slides were placed in an oven at 56° C. for 15 to 20 minutes for dewaxing and then soaked in Xylene solution for 5 minutes twice, followed by washing with 99% Ethanol for 1 to 3 minutes once. Perform tap water irrigation on the lower side of slides for 30 seconds. Soak the slides in Harris hematoxylin for 1 to 5 minutes. Perform tap water irrigation on the lower side of slides for another 30 seconds. Then, washed the slides with 50% and 70% ethanol for 1 minute, respectively. Soak the slides in 1% Eosin Y for 5 to 10 minutes, followed by washing with 75%, 80%, 90%, 95% ethanol for 1 minute, respectively. Soak the slides in 99% Ethanol/Xylene (1:1) for 1 minute. Soak the slides in Xylene solution for 5 minutes twice. The slides were mounted by use of mounting solution and then were put in a hood for dryness for 4 hours. A light microscope was used to inspect the slides.

3.2.3 Histological Study with Frozen Section and Gomori's Trichrome Staining

Gomori's trichrome is a staining procedure that combines the plasma stain (chromotrope 2R) and connective fiber stain (light green SF) in a phosphotungstic acid solution to which glacial acetic acid has been added. The staining method was selected to distinguish the nuclei (blue-black), cytoplasm (red) and collagen (green) in terms of the status of cell attachment, growth and distribution on the surface of the co-cultured skin model. To evaluate the histological change of the co-cultured biocomposite membrane by using the Gomori's trichrome staining method, the frozen section of the skin specimen of athymic mice was performed first, followed by fixing in methanol/acetone (1:1) solution for 30 minutes at 4° C., and then was rehydrated in descending alcohol solutions (100%×2, 90%, 80% and 70%) for 5 minutes each followed by rinsing with tap water. The sample was then immersed in Harris Hematoxylin for 5 minutes followed by washing in tap water until the water is clear. Thereafter, the sample was placed in Gomori's trichrome stain (solution A) for 25 minutes and then quickly rinsed off stain with distilled water followed by rinsing in solution B for 5 seconds. Finally, the sample was dehydrated in ascending alcohol solutions (95%× 2, 100%×2) for 5 minutes each, and then was placed onto a glass slide to be investigated under light microscope. Xylene was not used here due to adverse effect on the structure of collagen:PCL biocomposite film during staining procedure in this study.

3.2.4 Results

Figure 20:
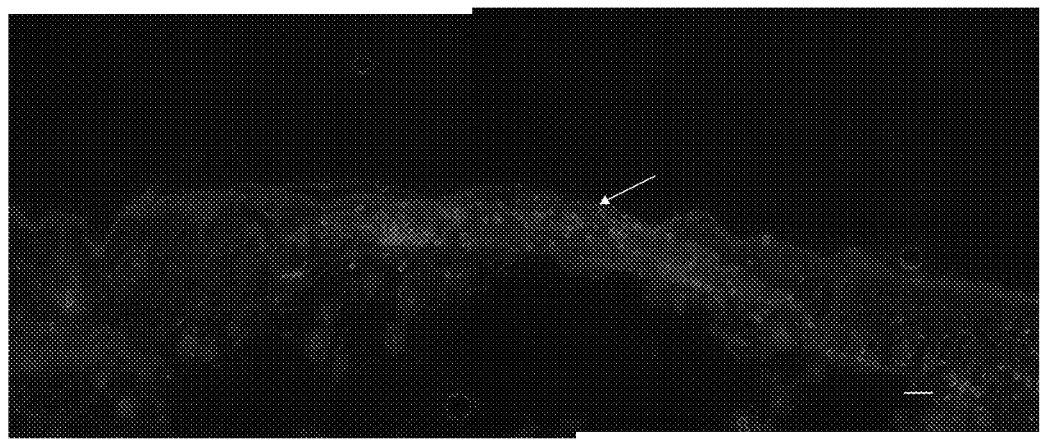
FIG. 20 illustrates the immunohistochemical staining of PHEK in the graft taken from an athymic mice that received treatment with artificial skin of Example 2 at a time interval up to 43 days, in which the primary monoclonal mouse anti-human involucrin antibody 1:20 and the secondary antibody of rhodamine-conjugated goat anti-mouse IgG 1:100 were used, strong red fluorescence of PHEK is indicated by an arrow (→), (100×, scale bar: 100 µm)
Figure 21:
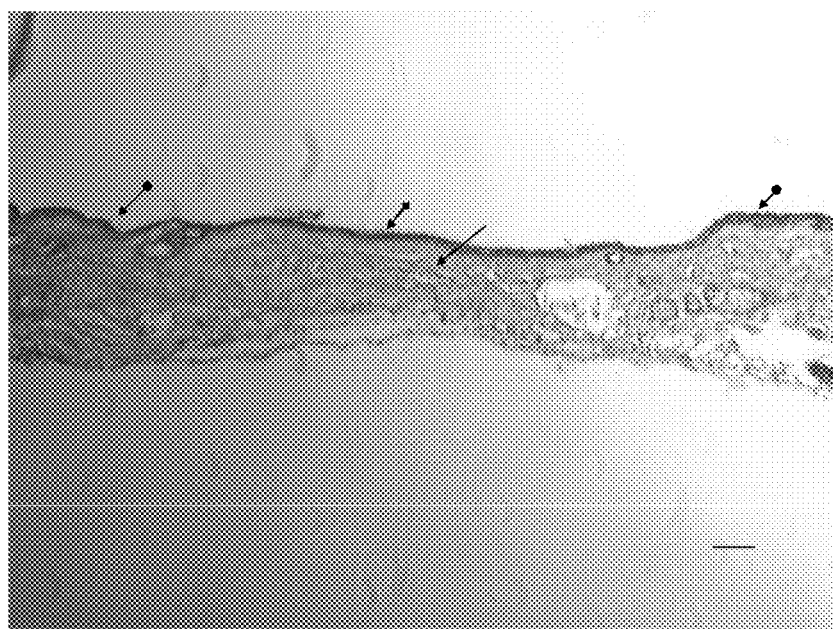
FIG. 21 is the photograph for H & E staining for the tissue sample taken from an athymic mice that received treatment with the artificial skin of Example 2 at a time interval up to 225 days, in which complete wound healing with differentiated epidermal layer (□→), newly formed hair follicle (→), and parallel arranged ECM formation were shown in the skin substitute engrafted between the normal skin structures of athymic mice (●→), (40×, scale bar: 100 µm)
Figure 22:
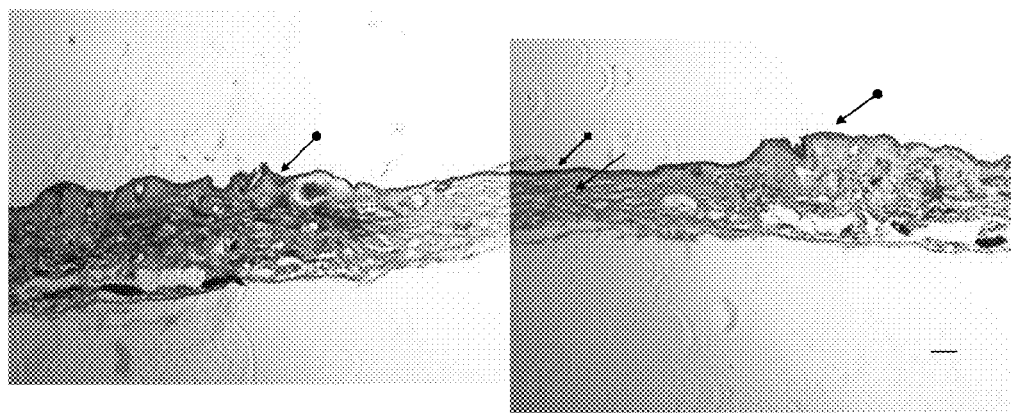
FIG. 22 is the photograph for Gomori's trichrome staining for the tissue sample taken from an athymic mice that received treatment with the artificial skin of Example 2 at a time interval up to 225 days, in which complete wound healing with differentiated epidermal layer (□→), and abundant collagen/ECM deposition (→; green color) were shown in the skin substitute engrafted between the normal skin structures of athymic mice (●→), (40×, scale bar: 100 µm)
Figure 23:
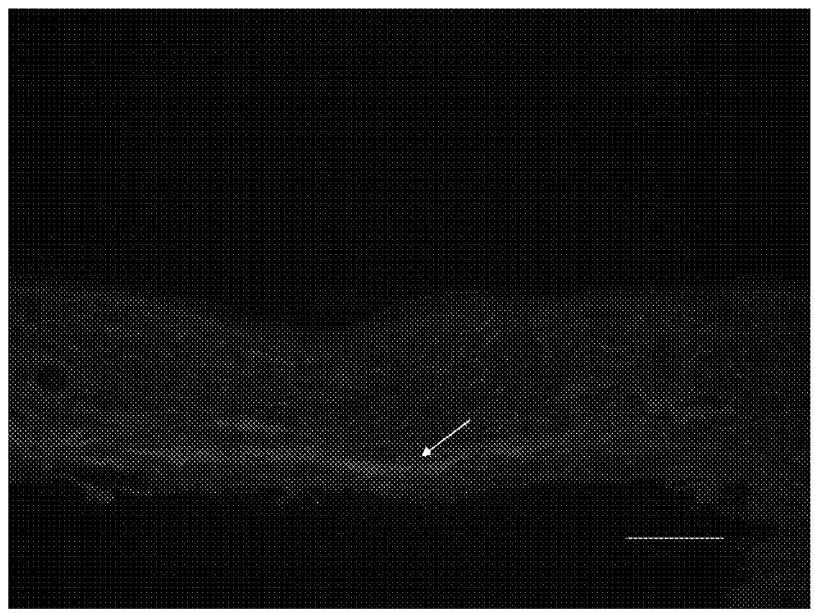
FIG. 23 illustrates the immunohistochemical staining of the surviving human originated fibroblasts/epithelial cells in the graft taken from the athymic mice receiving treatment with artificial skin of Example 2 at a time interval up to 225 days, in which labeling of PHEK and PHDF were confirmed by monoclonal mouse anti-human D7-FIB antibody 1:200 that will not cross-react with mouse or rat, and the secondary antibody of rhodamine-conjugated goat anti-mouse IgG 1:100; strong positive red fluorescence in the dermal layer of skin substitute is indicated by an arrow (→), (100×, scale bar: 100 µm)

FIG. 20 illustrates the immunochemical staining of PHEK in the transplanted artificial skin of Example 2 engrafted on the back of the athymic mice for a time interval up to 43 days, in which strong positive red fluorescent stain of PHEK is indicated by an arrow. Rapid wound coverage and healing with the formation of differentiated epidermal layer, abundant regular parallel-arranged collagen deposition in the dermal layer, and some newly formed hair follicular tissue over the marginal area of skin substitute (FIGS. 21 to 23). Furthermore, the survival of human-origin fibroblasts/epithelial cells in the graft at a time interval up to 225 days was further confirmed by labeling fibroblasts with monoclonal mouse anti-human D7-FIB antibody that will not cross-reacted with mouse or rat, and the secondary antibody of rhodamine-conjugated goat anti-mouse IgG in according to the procedures described above, further indicating a successful engrafting of the artificial skin of Example 2 in vivo, in which strong positive red fluorescent staining in the dermal layer of the artificial skin is indicated by the arrow (FIG. 23).

Figure 24:
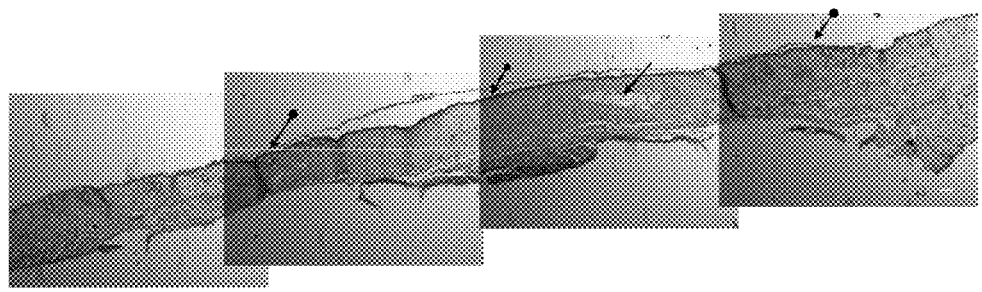
FIG. 24 is the photograph for H & E staining for the tissue sample taken from the athymic mice with retained open wound (i.e., mice that received no graft treatment) at a time interval up to 34 days, in which complete wound healing with differentiated epidermal layer (□→), and loose ECM formation (→) were shown in between the normal skin structures of athymic mice (●→), (40×, scale bar: 100 µm)
Figure 25:
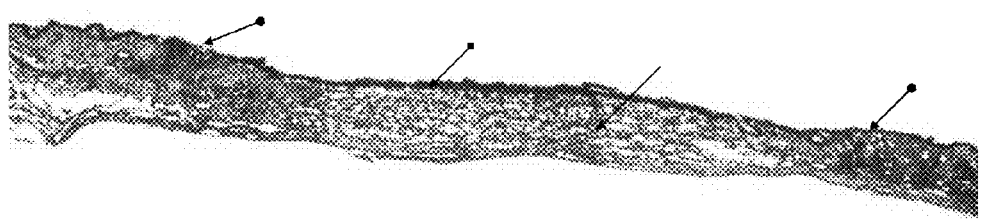
FIG. 25 is the photograph for Gomori's trichrome staining for the tissue sample taken from the athymic mice with retained open wound (i.e., mice that received no graft treatment) at a time interval up to 34 days, in which complete wound healing with differentiated epidermal layer (□→), and loose collagen deposition (→; green color) were shown in between the normal skin structures of athymic mice (●→), (40×, scale bar: 100 µm)
Figure 26:
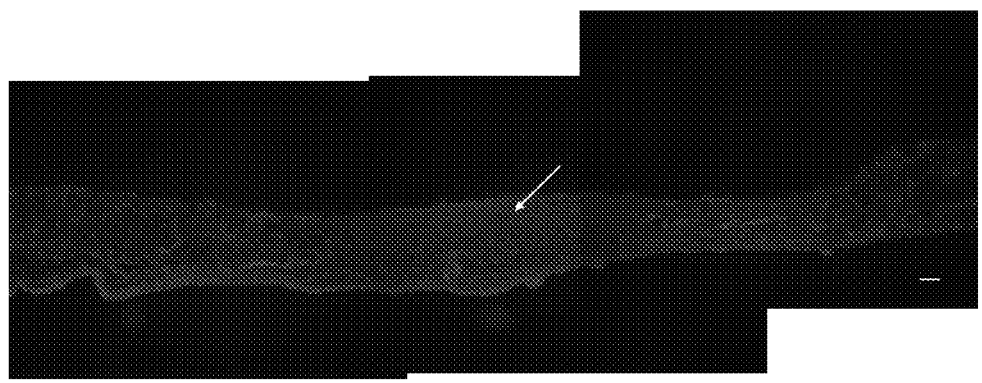
FIG. 26 illustrates the immunohistochemical staining of the tissue sample taken from the athymic mice with retained open wound (i.e., mice that received no graft treatment) at a time interval up to 34 days, in which labeling of PHEK and PHDF were confirmed by monoclonal mouse anti-human D7-FIB antibody 1:200 that will not cross-react with mouse or rat, and the secondary antibody of rhodamine-conjugated goat anti-mouse IgG 1:100; negative red fluorescence in the dermal layer at the surgical site is indicated by an arrow (→), (40×, scale bar: 100 µm)
Figure 27:
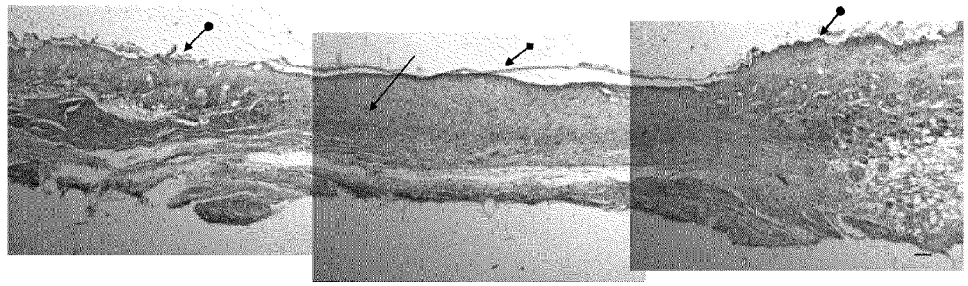
FIG. 27 is the photograph for H & E staining for the tissue sample taken from the athymic mice receiving blank biocomposite of Example 1.1 at a time interval up to 34 days, in which complete wound healing with differentiated epidermal layer (□→), and loose ECM formation (→) were shown in between the normal skin structures of athymic mice (●→, scale bar:100 µm)
Figure 28:
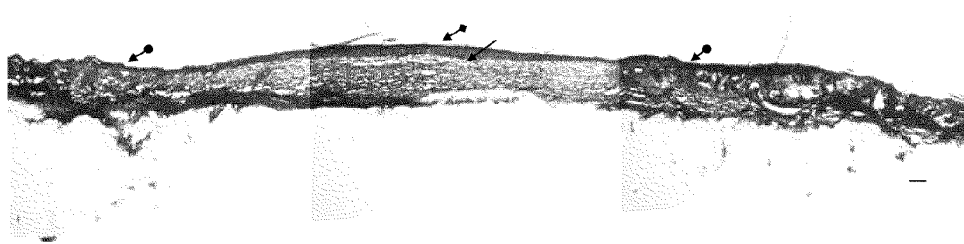
FIG. 28 is the photograph for Gomori's trichrome staining for the tissue sample taken from the athymic mice receiving blank biocomposite of Example 1.1 at a time interval up to 34 days, in which complete wound healing with differentiated epidermal layer (□→), and abundant collagen deposition (→; green color) were shown in between the normal skin structures of athymic mice (●→), (100×, scale bar:100 µm)
Figure 29:
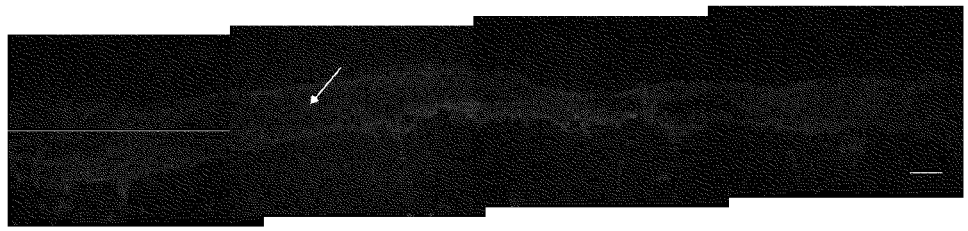
FIG. 29 illustrates the immunohistochemical staining of the tissue sample taken from the athymic mice receiving blank biocomposite of Example 1.1 at a time interval up to 34 days, in which labeling of PHEK and PHDF were confirmed by monoclonal mouse anti-human D7-FIB antibody 1:200 that will not cross-react with mouse or rat, and the secondary antibody of rhodamine-conjugated goat anti-mouse IgG 1:100, and negative red fluorescence is shown in the dermal layer of the surgical site (→), (100×, scale bar:100 µm).

However, for the group of mice that did not receive any graft treatment, i.e., mice with retained open wound, these mice showed a relatively slower wound healing process with the formation of thin differentiated epidermal layer, loose collagen/ECM deposition in the dermal layer, and no newly formed hair follicular tissue were found in the skin substitute (FIGS. 24 to 26). In addition, human-origin fibroblasts/epithelial cells were absent from the surgical site on the back of any of the mice (FIG. 26). In contrast, the group of mice that received blank biocomposite of example 1.1 showed a relatively more rapid wound healing process with the formation of differentiated epidermal layer, with more deposition of collagen/ECM in the dermal layer, and some newly formed hair follicular tissue were identified at the margin of the skin substitute (FIGS. 27 to 29). Moreover, nor is there any human-origin fibroblasts/epithelial cells found at the surgical site on the back skin of the experimental animal (FIG. 29), which is same as that in the group of mice with retained open wounds.

INDUSTRIAL APPLICABILITY

It is an advantage of the present invention that it provides a skin substitute, which may be an acellular biocomposite membrane, comprising PCL and at least one material selected from collagen and gelatin; or an artificial skin, comprising living cells cultivated on both sides of the biocomposite membrane. In a preferred example, the acellular biocomposite membrane is made out of PCL and a less expensive material, gelatin, in place of collagen. The cost of gelatin/10% collagen:PCL biocomposites is about one tenth of that of collagen:PCL biocomposites, yet it exhibits the same effects as that of pure collagen group, thereby making gelatin an extremely competitive biomaterial for use in manufacturing skin substitutes. The acellular biocomposite membrane of this invention is easy to make and use, and store for a long period of time, and can be applied directly onto a skin wound as a dressing. The artificial skin comprises living cells grown on both sides of the biocomposite membrane may also be used in vitro for drug screening purposes or in vivo for repairing skin damages. In a preferred example, the artificial skin comprises keratinocytes on one side of the biocomposite membrane, and fibroblasts on the other side of the membrane.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A porous biocomposite membrane for promoting at least one of wound healing and tissue regeneration, comprising poly(E-caprolactone) (PCL) and gelatin in a weight ratio between 4:1 to 20:1, with the proviso that collagen is not present in the biocomposite membrane, wherein the biocomposite membrane is obtained by a method comprising:
   providing a freeze-dried gelatin mat; and
   pouring a poly (e-caprolactone) solution onto the freeze-dried gelatin mat and subsequently evaporating the solvent therein to form the porous biocomposite membrane.

2. An artificial skin for grafting onto a subject in need of at least one of skin treatment and wound coverage, comprising:
   the biocomposite membrane of claim 1;
   a layer of keratinocytes on one side of the biocomposite membrane; and
   a layer of fibroblasts on the other side of the biocomposite membrane.

3. The artificial skin of claim 2, wherein the cells are of mammalian origin, and the cells being normal, genetically modified or malignant.

4. The artificial skin of claim 3, wherein the mammalian origin is human.

5. The artificial skin of claim 2, wherein the subject in need of at least one of skin treatment and wound coverage is the one with ear drum defect, disruption of tendon/nerve and/or skin damage that includes burn injuries, ulcers, impaired pigmentation, excisions or other dermatological conditions.

6. A method for cultivating an artificial skin for grafting onto a subject in need of at least one of skin treatment and wound coverage, comprising:
   growing a layer of keratinocytes on one side of the biocomposite membrane of claim 2; and
   growing a layer of fibroblasts on the other side of the biocomposite membrane of claim 2.

7. The method of claim 6, wherein the step of growing a layer of keratinocytes is performed before or after the step of growing a layer of fibroblasts.

8. The method of claim 6, wherein the cells are of mammalian origin.

9. The method of claim 8, wherein the cells are from human.

10. The method of claim 6, wherein the subject in need of at least one of skin treatment and wound coverage is the one with ear drum defect, disruption of tendon/nerve and/or skin damage that includes burn injuries, ulcers, impaired pigmentation, excisions or other dermatological conditions.

11. An artificial skin prepared in accordance with the method of claim 6.

12. A biocomposite product, comprising:
   the biocomposite membrane of claim 1; and
   at least one layer of cells grown on at least one side of the biocomposite membrane;
   wherein the cells are selected from the group consisting of fibroblasts, keratinocytes, melanocytes, cells originated from hair follicle and/or sweat gland, endothelial cells originated from the blood, blood cells, chondrocytes, osteocytes, osteoblasts and stem cells originated from the cord blood and/or bone marrow, and the cells being normal, genetically modified or malignant.

13. The biocomposite product of claim 12, wherein the biocomposite membrane comprises two layers of cells, with each layer being grown on one side of the membrane.

14. The biocomposite product of claim 13, wherein one layer of cells is keratinocytes, and the other layer of cells is fibroblasts.

15. The biocomposite product of claim 12, wherein the biocomposite product is useful for grafting onto a subject in need of skin treatment and/or wound coverage.

16. The biocomposite product of claim 15, wherein the subject in need of skin treatment and/or wound coverage is the one with ear drum defect, disruption of tendon/nerve and/or skin damage that includes burn injuries, ulcers, impaired pigmentation, excisions or other dermatological conditions.

* * * * *